(12) United States Patent
Kadler et al.

(10) Patent No.: US 7,351,552 B2
(45) Date of Patent: Apr. 1, 2008

(54) MODIFIED PRO-α PEPTIDES AND THEIR USES

(75) Inventors: Karl Kadler, Stockport (GB); Neil Bulleid, Stockport (GB); Gillian Ashcroft, Wrightington (GB)

(73) Assignee: The University of Manchester, Manchester (GB)

( * ) Notice: Subject to any disclaimer, the term of this patent is extended or adjusted under 35 U.S.C. 154(b) by 152 days.

(21) Appl. No.: 10/554,068

(22) PCT Filed: Apr. 21, 2004

(86) PCT No.: PCT/GB2004/001719

§ 371 (c)(1),
(2), (4) Date: Oct. 21, 2005

(87) PCT Pub. No.: WO2004/094472

PCT Pub. Date: Nov. 4, 2004

(65) Prior Publication Data

US 2007/0031478 A1 Feb. 8, 2007

(30) Foreign Application Priority Data

Apr. 22, 2003 (GB) .................................. 0309064

(51) Int. Cl.
*C12P 21/06* (2006.01)
*C07K 14/00* (2006.01)
*C07H 17/00* (2006.01)

(52) U.S. Cl. .................. 435/69.1; 435/320.1; 435/325; 536/23.1; 530/350

(58) Field of Classification Search ............... 435/69.1, 435/320.1, 325; 536/23.1; 530/350
See application file for complete search history.

(56) References Cited

U.S. PATENT DOCUMENTS 5,266,328 A 11/1993 Skubitz et al.
6,277,600 B1 * 8/2001 Tomita et al. ............. 435/69.7

FOREIGN PATENT DOCUMENTS

| EP | 0 704 532 A2 | 4/1996 |
| EP | 0 747 068 A1 | 12/1996 |
| EP | 0 985 732 A2 | 3/2000 |
| GB | 2 400 852 A | 10/2004 |
| WO | WO 99/08311 | 2/1999 |
| WO | WO 03/035692 A2 | 5/2003 |

* cited by examiner

*Primary Examiner*—Karen Cochrane Carlson
(74) *Attorney, Agent, or Firm*—Bose McKinney & Evans, LLP

(57) ABSTRACT

A modified pro-α chain comprising a triple helix forming domain linked to a polypeptide from at least part of a laminin glycoprotein. The pro-α chain may form part of a procollagen molecule that has the N-terminal domain retained. The procollagen molecules may be incorporated into collagen polymers, matrices and gels and be used for such applications as wound healing.

88 Claims, 15 Drawing Sheets

```
                                        atgatgagct tgtgcaaaa ggggagctgg
ctacttctcg ctctgcttca tcccactatt attttggcaa catctctgtc cttgtttctc
caaaggccca actcaagaga aaatggggt actgagaata tgtttgtgat gtaccttgga
aataaagatg cctcccggga ctacatcggc atggcagttg tggatggcca gctcacctgt
gtctacaacc tgggggaccg tgaggctgaa ctccaagtgg accagatctt gaccaagagt
gagactaagg aggcagttat ggatcgggtg aaatttcaga gaatttatca gtttgcaagg
cttaattaca ccaaaggagc cacatccagt aaaccagaaa cacccggagt ctatgacatg
gatggtagaa atagcaatac actccttaat ttggatcctg aaaatgttgt attttatgtt
ggaggttacc cacctgattt taaacttccc agtcgactaa gtttccctcc atacaaaggt
tgtattgaat tagatgacct caatgaaaat gttctgagct tgtacaactt caaaaaaaca
ttcaatctca acacaactga agtggagcct tgtagaagga ggaaggaaga gtcagacaaa
aattattttg aaggtacggg ctatgctcga gttccaactc aaccacatgc tcccatccca
accttggac agacaattca gaccaccgtg atagaggct tgctgttctt tgcagaaaac
ggggatcgct tcatatctct aaatatagaa gatggcaagc tcatggtgag atacaaactg
aattcagagc taccaaaaga gagaggagtt ggagacgcca taaacaacgg cagagaccat
tcgattcaga tcaaaattgg aaaactccaa aagcgtatgt ggataaatgt ggacgttcaa
aacactataa ttgatggtga agtatttgat ttcagcacat attatctggg aggaattcca
attgcaatca gggaaagatt taacatttct acgcctgctt tccgaggctg catgaaaaat
ttgaagaaaa ccagtggtgt cgttagattg aatgatactg tgggagtaac caaaaagtgc
tcggaagact ggaagcttgt gcgatctgcc tcattctcca gaggaggaca attgagtttc
actgatttgg gcttaccacc tactgaccac ctccaggcct catttggatt tcagaccttt
caacccagtg gcatattat agatcatcag acatggacaa ggaacctgca ggtcactctg
gaagatggtt acattgaatt gagcaccagc gatagcggcg gcccaatttt taaatctcca
cagacgtata tggatggttt actgcattat gtatctgtaa taagcgacaa ctctggacta
cggcttctca tcgatgacca gcttctgaga aatagcaaaa ggctaaaaca catttcaagt
tcccggcagt ctctgcgtct gggcgggagc aattttgagg gttgtattag caatgttttt
gtccagaggt tatcactgag tcctgaagtc ctagatttga ccagtaactc tctcaagaga
gatgtgtccc tgggaggctg cagtttaaac aaaccacctt ttctaatgtt gcttaaaggt
tctaccaggt ttaacaagac caagactttt cgtatcaacc agctgttgca ggacacacca
gtggcctccc caaggagcgt gaaggtgtgg caagatgcta atggtcaagg acctcaaggc
cccaagggag atccaggccc tcctggtatt cctgggagaa atggtgaccc tggtattcca
ggacaaccag ggtcccctgg ttctcctggc cccctggaa tctgtgaatc atgccctact
ggtcctcaga actattctcc ccagtatgat tcatatgatg tcaagtctgg agtagcagta
ggaggactcg caggctatcc tggaccagct ggcccccag gccctcccgg tccccctggt
acatctggtc atcctggttc ccctggatct ccaggatacc aaggaccccc tggtgaacct
gggcaagctg gtccttcagg ccctccagga cctcctggtg ctataggtcc atctggtcct
gctggaaaag atggagaatc aggtagaccc ggacgacctg gagcgagg attgcctgga
cctccaggta tcaaaggtcc agctgggata cctggattcc ctggtatgaa aggacacaga
ggcttcgatg gacgaaatgg agaaaagggt gaaacaggtg ctcctggatt aaagggtgaa
aatggtcttc caggcgaaaa tggagctcct ggacccatgg gtccaagagg ggctcctggt
gagcgaggac ggccaggact tcctggggct gcaggtgctc ggggtaatga cggtgctcga
ggcagtgatg gtcaaccagg ccctcctggt cctcctggaa ctgccggatt ccctggatcc
cctggtgcta agggtgaagt tggacctgca gggtctcctg gttcaaatgg tgcccctgga
caaagaggag aacctggacc tcagggacac gctggtgctc aaggtcctcc tggccctcct
gggattaatg gtagtcctgg tggtaaaggc gaaatgggtc ccgctggcat tcctggagct
cctggactga tgggagcccg gggtcctcca ggaccagccg gtgctaatgg tgctcctgga
ctgcgaggtg gtgcaggtga gcctggtaag aatggtgcca aggagagcc cggaccacgt
ggtgaacgcg gtgaggctgg tattccaggt gttccaggag ctaaaggcga agatggcaag
gatggatcac ctggagaacc tggtgcaaat gggcttccag gagctgcagg agaaagggt
gcccctgggt tccgaggacc tgctggacca aatggcatcc aggagaaaa gggtcctgct
ggagagcgtg tgctccagg ccctgcaggg cccagaggag ctgctggaga acctggcaga
gatggcgtcc ctggaggtcc aggaatgagg ggcatgcccg aagtccagg aggaccagga
agtgatggga accagggcc tcccggaagt caaggagaaa gtggtcgacc aggtcctcct
gggccatctg gtccccgagg tcagcctggt gtcatgggct ccccggtcc taaaggaaat
```

FIG. 3

```
gatggtgctc ctggtaagaa tggagaacga ggtggccctg gaggacctgg ccctcagggt
cctcctggaa agaatggtga aactggacct caaggacccc cagggcctac tgggcctggt
ggtgacaaag gagacacagg accccctggt ccacaaggat tacaaggctt gcctggtaca
ggtggtcctc caggagaaaa tggaaaacct ggggaaccag gtccaaaggg tgatgccggt
gcacctggag ctccaggagg caagggtgat gctggtgccc ctggtgaacg tggacctcct
ggattggcag gggccccagg acttagaggt ggagctggtc cccctggtcc cgaaggagga
aagggtgctg ctggtcctcc tgggccacct ggtgctgctg gtactcctgg tctgcaagga
atgcctggag aaagaggagg tcttggaagt cctggtccaa agggtgacaa gggtgaacca
ggcggcccag gtgctgatgg tgtcccaggg aaagatggcc caaggggtcc tactggtcct
attggtcctc ctggcccagc tggccagcct ggagataagg gtgaaggtgg tgccccgga
cttccaggta tagctggacc tcgtggtagc cctggtgaga gaggtgaaac tggccctcca
ggacctgctg gtttcctgg tgctcctgga cagaatggtg aacctggtgg taaggagaa
agagggctc cgggtgagaa aggtgaagga ggccctcctg gagttgcagg accccctgga
ggttctggac ctgctggtcc tcctggtccc caaggtgtca aaggtgaacg tggcagtcct
ggtggacctg gtgctgctgg cttccctggt gctcgtggtc ttcctggtcc tcctggtagt
aatggtaacc caggaccccc aggtccagc ggttctccag gcaaggatgg gcccccaggt
cctgcgggta acactggtgc tcctggcagc cctggagtgt ctggaccaaa aggtgatgct
ggccaaccag gagagaaggg atcgcctggt gcccagggcc caccaggagc tccaggccca
cttgggattg ctgggatcac tggagcacgg ggtcttgcag gaccaccagg catgccaggt
cctaggggaa gccctggccc tcagggtgtc aagggtgaaa gtgggaaacc aggagctaac
ggtctcagtg gagaacgtgg tccccctgga ccccagggtc ttcctggtct ggctggtaca
gctggtgaac ctggaagaga tggaaaccct ggatcagatg gtcttccagg ccgagatgga
tctcctggtg gcaagggtga tcgtggtgaa aatggctctc tggtgccccc tggcgctcct
ggtcatccag gcccacctgg tcctgtcggt ccagctggaa agagtggtga cagaggagaa
agtggccctg ctggccctgc tggtgctccc ggtcctgctg gttcccgagg tgctcctggt
cctcaaggcc cacgtggtga caaaggtgaa acaggtgaac gtggagctgc tggcatcaaa
ggacatcgag gattccctgg taatccaggt gccccaggtt ctccaggccc tgctggtcag
cagggtgcaa tcggcagtcc aggacctgca ggccccagag gacctgttgg acccagtgga
cctcctggca aagatggaac cagtggacat ccaggtccca ttggaccacc agggcctcga
ggtaacagag gtgaaagagg atctgagggc tccccaggcc accagggca accaggccct
cctggacctc ctggtgcccc tggtcccttg tgtggtggtg ttggagccgc tgccattgct
gggattggag gtgaaaaagc tggcggtttt gccccgtatt atggagatga accaatggat
ttcaaaatca acaccgatga gattatgact tcactcaagt ctgttaatgg acaaatagaa
agcctcatta gtcctgatgg ttctcgtaaa aaccccgcta gaaactgcag agacctgaaa
ttctgccatc ctgaactcaa gagtggagaa tactgggttg acccctaacca aggatgcaaa
ttggatgcta tcaaggtatt ctgtaatatg gaaactgggg aaacatgcat aagtgccaat
cctttgaatg ttccacggaa acactggtgg acagattcta gtgctgagaa gaaacacgtt
tggtttggag agtccatgga tggtggtttt cagtttagct acggcaatcc tgaacttcct
gaagatgtcc ttgatgtgca gctggcattc cttcgacttc tctccagccg agcttccag
aacatcacat atcactgcaa aaatagcatt gcatacatgg atcaggccag tggaaatgta
aagaaggccc tgaagctgat ggggtcaaat gaaggtgaat tcaaggctga aggaaatagc
aaattcacct acacagttct ggaggatggt tgcacgaaac acactgggga atggagcaaa
acagtctttg aatatcgaac acgcaaggct gtgagactac ctattgtaga tattgcaccc
tatgacattg gtggtcctga tcaagaattt ggtgtggacg ttggccctgt ttgctttta
taa
```

```
                                                                At gatgagcttt
gtgcaaaagg ggagctggct acttctcgct ctgcttcatc ccactattat tttggcatgc
tcggaagact ggaagcttgt gcgatctgcc tcattctcca gaggaggaca attgagtttc
actgatttgg gcttaccacc tactgaccac ctccaggcct catttggatt tcagacccttt
caacccagtg gcatattatt agatcatcag acatggacaa ggaacctgca ggtcactctg
gaagatggtt acattgaatt gagcaccagc gatagcggcg gcccaatttt taaatctcca
cagacgtata tggatggttt actgcattat gtatctgtaa taagcgacaa ctctggacta
cggcttctca tcgatgacca gcttctgaga aatagcaaaa ggctaaaaca catttcaagt
tcccggcagt ctctgcgtct gggcgggagc aattttgagg gttgtattag caatgttttt
gtccagaggt tatcactgag tcctgaagtc ctagatttga ccagtaactc tctcaagaga
gatgtgtccc tgggaggctg cagtttaaac aaaccacctt ttctaatgtt gcttaaaggt
tctaccaggt ttaacaagac caagactttt cgtatcaacc agctgttgca ggacacacca
gtggcctccc caaggagcgt gaaggtgtgg caagatgcta atggtcaagg acctcaaggc
cccaagggag atccaggccc tcctggtatt cctgggagaa atggtgaccc tggtattcca
ggacaaccag ggtcccctgg ttctcctggc ccccctggaa tctgtgaatc atgccctact
ggtcctcaga actattctcc ccagtatgat tcatatgatg tcaagtctgg agtagcagta
ggaggactcg caggctatcc tggaccagct ggccccccag gccctcccgg tcccccctggt
acatctggtc atcctggttc ccctggatct ccaggatacc aaggaccccc tggtgaacct
gggcaagctg gtccttcagg ccctccagga cctcctggtg ctataggtcc atctggtcct
gctggaaaag atggagaatc aggtagaccc ggacgacctg gagagcgagg attgcctgga
cctccaggta tcaaaggtcc agctgggata cctggattcc ctggtatgaa aggacacaga
ggcttcgatg gacgaaatgg agaaaaggt gaaacaggtg ctcctggatt aaagggtgaa
aatggtcttc caggcgaaaa tggagctcct ggacccatgg gtccaagagg ggctcctggt
gagcgaggac ggccaggact tcctggggct gcaggtgctc ggggtaatga cggtgctcga
ggcagtgatg gtcaaccagg ccctcctggt cctcctggaa ctgccggatt ccctggatcc
cctggtgcta agggtgaagt tggacctgca gggtctcctg gttcaaatgg tgccccctgga
caaagaggag aacctggacc tcagggacac gctggtgctc aaggtcctcc tggcccctct
gggattaatg gtagtcctgg tggtaaaggc gaaatgggtc ccgctggcat tcctggagct
cctggactga tgggagcccg gggtcctcca ggaccagccg gtgctaatgg tgctcctgga
ctgcgaggtg gtgcaggtga gcctggtaag aatggtgcca aaggagagcc cggaccacgt
ggtgaacgcg gtgaggctgg tattccaggt gttccaggag ctaaaggcga agatggcaag
gatggatcac ctggagaacc tggtgcaaat gggcttccag gagctgcagg agaaaggggt
gcccctgggt tccgaggacc tgctggacca aatggcatcc caggagaaaa gggtcctgct
ggagagcgtg gtgctccagg ccctgcaggg cccagaggag ctgctggaga acctggcaga
gatggcgtcc ctggaggtcc aggaatgagg ggcatgcccg gaagtccagg aggaccagga
agtgatggga aaccagggcc tcccggaagt caaggagaaa gtggtcgacc aggtcctcct
gggccatctg gtccccgagg tcagcctggt gtcatgggct tccccggtcc taaaggaaat
gatggtgctc ctggtaagaa tggagaacga ggtggccctg gaggacctgg ccctcagggt
cctcctggaa agaatggtga aactggacct caaggacccc cagggcctac tgggcctggt
ggtgacaaag agacacagg accccctggt ccacaaggat tacaaggctt gcctggtaca
ggtggtcctc caggagaaaa tggaaaacct ggggaaccag gtccaaaggg tgatgccggt
gcacctggag ctccaggagg caagggtgat gctggtgccc ctggtgaacg tggacctcct
ggattggcag gggcccccagg acttagaggt ggagctggtc cccctggtcc cgaaggagga
aagggtgctg ctggtcctcc tgggccacct ggtgctgctg gtactcctgg tctgcaagga
atgcctggag aaagaggagg tcttggaagt cctggtccaa agggtgacaa gggtgaacca
ggcggcccag gtgctgatgg tgtcccaggg aaagatggcc caaggggtcc tactggtcct
attggtcctc ctggcccagc tggccagcct ggagataagg gtgaaggtgg tgcccccgga
cttccaggta tagctggacc tcgtggtagc cctggtgaga gaggtgaaac tggccctcca
ggacctgctg gtttccctgg tgctcctgga cagaatggtg aacctggtgg taaaggagaa
agagggctc cgggtgagaa aggtgaagga ggccctcctg gagttgcagg acccctggga
ggttctggac ctgctggtcc tcctggtccc aaggtgtca aaggtgaacg tggcagtcct
ggtggacctg gtgctgctgg cttccctggt gctcgtggtc ttcctggtcc tcctggtagt
aatggtaacc caggaccccc aggtccaagc ggttctccag gcaaggatgg gcccccaggt
cctgcgggta caacactggtgc tcctggcagc cctggagtgt ctggaccaaa aggtgatgct
```

FIG. 6

```
ggccaaccag gagagaaggg atcgcctggt gcccagggcc caccaggagc tccaggccca
cttgggattg ctgggatcac tggagcacgg ggtcttgcag gaccaccagg catgccaggt
cctagggaa  gccctggccc tcagggtgtc aagggtgaaa gtgggaaacc aggagctaac
ggtctcagtg gagaacgtgg tccccctgga ccccagggtc ttcctggtct ggctggtaca
gctggtgaac ctggaagaga tggaaaccct ggatcagatg gtcttccagg ccgagatgga
tctcctggtg gcaagggtga tcgtggtgaa aatggctctc ctggtgcccc tggcgctcct
ggtcatccag gcccacctgg tcctgtcggt ccagctggaa agagtggtga cagaggagaa
agtggccctg ctggccctgc tggtgctccc ggtcctgctg gttcccgagg tgctcctggt
cctcaaggcc cacgtggtga caaaggtgaa acaggtgaac gtggagctgc tggcatcaaa
ggacatcgag gattccctgg taatccaggt gccccaggtt ctccaggccc tgctggtcag
cagggtgcaa tcggcagtcc aggacctgca ggccccagag gacctgttgg acccagtgga
cctcctggca aagatggaac cagtggacat ccaggtccca ttggaccacc agggcctcga
ggtaacagag gtgaaagagg atctgagggc tccccaggcc acccagggca accaggccct
cctggacctc ctggtgcccc tggtccttgc tgtggtggtg ttggagccgc tgccattgct
gggattggag gtgaaaaagc tggcggtttt gccccgtatt atggagatga accaatggat
ttcaaaatca acaccgatga gattatgact tcactcaagt ctgttaatgg acaaatagaa
agcctcatta gtcctgatgg ttctcgtaaa aaccccgcta gaaactgcag agacctgaaa
ttctgccatc ctgaactcaa gagtggagaa tactgggttg accctaacca aggatgcaaa
ttggatgcta tcaaggtatt ctgtaatatg gaaactgggg aaacatgcat aagtgccaat
cctttgaatg ttccacggaa acactggtgg acagattcta gtgctgagaa gaaacacgtt
tggtttggag agtccatgga tggtggtttt cagtttagct acggcaatcc tgaacttcct
gaagatgtcc ttgatgtgca gctggcattc cttcgacttc tctccagccg agcttcccag
aacatcacat atcactgcaa aaatagcatt gcatacatgg atcaggccag tggaaatgta
aagaaggccc tgaagctgat ggggtcaaat gaaggtgaat tcaaggctga aggaaatagc
aaattcacct acacagttct ggaggatggt tgcacgaaac acactgggga atggagcaaa
acagtctttg aatatcgaac acgcaaggct gtgagactac ctattgtaga tattgcaccc
tatgacattg gtggtcctga tcaagaattt ggtgtggacg ttggccctgt ttgcttttta
taa
```

FIG. 6 cont;

```
MMSFVQKGSWLLLALLHPTIILACSEDWKLV
RSASFSRGGQLSFTDLGLPPTDHLQASFGFQ
TFQPSGILLDHQTWTRNLQVTLEDGYIELST
SDSGGPIFKSPQTYMDGLLHYVSVISDNSGL
RLLIDDQLLRNSKRLKHISSSRQSLRLGGSN
FEGCISNVFVQRLSLSPEVLDLTSNSLKRDV
SLGGCSLNKPPFLMLLKGSTRFNKTKTFRIN
QLLQDTPVASPRSVKVWQDANGQGPQGPKGD
PGPPGIPGRNGDPGIPGQPGSPGSPGPPGIC
ESCPTGPQNYSPQYDSYDVKSGVAVGGLAGY
PGPAGPPGPPGPPGTSGHPGSPGSPGYQGPP
GEPGQAGPSGPPGPPGAIGPSGPAGKDGESG
RPGRPGERGLPGPPGIKGPAGIPGFPGMKGH
RGFDGRNGEKGETGAPGLKGENGLPGENGAP
GPMGPRGAPGERGRPGLPGAAGARGNDGARG
SDGQPGPPGPPGTAGFPGSPGAKGEVGPAGS
PGSNGAPGQRGEPGPQGHAGAQGPPGPPGIN
GSPGGKGEMGPAGIPGAPGLMGARGPPGPAG
ANGAPGLRGGAGEPGKNGAKGEPGPRGERGE
AGIPGVPGAKGEDGKDGSPGEPGANGLPGAA
GERGAPGFRGPAGPNGIPGEKGPAGERGAPG
PAGPRGAAGEPGRDGVPGGPGMRGMPGSPGG
PGSDGKPGPPGSQGESGRPGPPGPSGPRGQP
GVMGFPGPKGNDGAPGKNGERGGPGGPGPQG
PPGKNGETGPQGPPGPTGPGGDKGDTGPPGP
QGLQGLPGTGGPPGENGKPGEPGPKGDAGAP
GAPGGKGDAGAPGERGPPGLAGAPGLRGGAG
PPGPEGGKGAAGPPGPPGAAGTPGLQGMPGE
RGGLGSPGPKGDKGEPGGPGADGVPGKDGPR
GPTGPIGPPGPAGQPGDKGEGGAPGLPGIAG
PRGSPGERGETGPPGPAGFPGAPGQNGEPGG
KGERGAPGEKGEGGPPGVAGPPGGSGPAGPP
GPQGVKGERGSPGGPGAAGFPGARGLPGPPG
SNGNPGPPGPSGSPGKDGPPGPAGNTGAPGS
PGVSGPKGDAGQPGEKGSPGAQGPPGAPGPL
GIAGITGARGLAGPPGMPGPRGSPGPQGVKG
ESGKPGANGLSGERGPPGPQGLPGLAGTAGE
PGRDGNPGSDGLPGRDGSPGGKGDRGENGSP
GAPGAPGHPGPPGPVGPAGKSGDRGESGPAG
PAGAPGPAGSRGAPGPQGPRGDKGETGERGA
AGIKGHRGFPGNPGAPGSPGPAGQQGAIGSP
GPAGPRGPVGPSGPPGKDGTSGHPGPIGPPG
PRGNRGERGSEGSPGHPGQPGPPGPPGAPGP
CCGGVGAAAIAGIGGEKAGGFAPYYGDEPMD
FKINTDEIMTSLKSVNGQIESLISPDGSRKN
PARNCRDLKFCHPELKSGEYWVDPNQGCKLD
AIKVFCNMETGETCISANPLNVPRKHWWTDS
SAEKKHVWFGESMDGGFQFSYGNPELPEDVL
DVQLAFLRLLSSRASQNITYHCKNSIAYMDQ
ASGNVKKALKLMGSNEGEFKAEGNSKFTYTV
LEDGCTKHTGEWSKTVFEYRTRKAVRLPIVD
IAPYDIGGPDQEFGVDVGPVCFL
```

FIG. 7

```
atgaagtc    cagcggcctc  ttccccttcc  tggtgctgct  tgccctggga
actctggcac  cttgggctgt  ggaaggctct  ggaaagtcct  tcaaagctgg
agtctgtcct  cctaagaaat  ctgcccagtg  ccttagatac  aagaaacctg
agtgccagag  tgactggcag  tgtccaggga  agaagagatg  ttgtcctgac
acttgtggca  tcaaatgcct  ggatcctgtt  gacacccaa   acccaacaag
gaggaagcct  gggaagtgcc  cagtgactta  tggccaatgt  ttgatgctta
accccccaa   tttctgtgag  atggatggcc  agtgcaagcg  tgacttgaag
tgttgcatgg  gcatgtgtgg  gaaatcctgc  gtttccctg   tgaaagct gctgt       tgaaggagga  tgttcccatc  ttggtcagtc  ctatgcggat
agagatgtct  ggaagccaga  accatgccaa  atatgtgtct  gtgactcagg
atccgttctc  tgcgatgaca  taatatgtga  cgatcaagaa  ttagactgcc
ccaacccaga  aattccattt  ggagaatgtt  gtgcagtttg  cccacagcct
ccaactgctc  ctactcgccc  tcctaatggt  caaggacctc  aaggccccaa
gggagatcca  ggccctcctg  gtattcctgg  gagaaatggt  gaccctggta
ttccaggaca  accagggtcc  cctggttctc  ctggcccccc  tggaatctgt
gaatcatgcc  ctactggtcc  tcagaactat  tctcccagt   atgattcata
tgatgtcaag  tctggagtag  cagtaggagg  actcgcaggc  tatcctggac
cagctggccc  cccaggccct  cccggtcccc  ctggtacatc  tggtcatcct
ggttccctg   gatctccagg  ataccaagga  cccctggtg   aacctgggca
agctggtcct  tcaggccctc  caggacctcc  tggtgctata  ggtccatctg
gtcctgctgg  aaaagatgga  gaatcaggta  gacccggacg  acctggagag
cgaggattgc  ctggacctcc  aggtatcaaa  ggtccagctg  ggatacctgg
attccctggt  atgaaaggac  acagaggctt  cgatggacga  aatggagaaa
agggtgaaac  aggtgctcct  ggattaaagg  gtgaaatgg   tcttccaggc
gaaaatggag  ctcctggacc  catgggtcca  agagggctc   ctggtgagcg
aggacggcca  ggacttcctg  gggctgcagg  tgctcggggt  aatgacggtg
ctcgaggcag  tgatggtcaa  ccaggccctc  ctggtcctcc  tggaactgcc
ggattccctg  gatcccctgg  tgctaagggt  gaagttggac  ctgcagggtc
tcctggttca  aatggtgccc  ctggacaaag  aggagaacct  ggacctcagg
gacacgctgg  tgctcaaggt  cctcctggcc  ctcctgggat  taatggtagt
cctggtggta  aaggcgaaat  gggtcccgct  ggcattcctg  gagctcctgg
actgatggga  gcccggggtc  ctccaggacc  agccggtgct  aatggtgctc
ctggactgcg  aggtggtgca  ggtgagcctg  gtaagaatgg  tgccaaagga
gagcccggac  cacgtggtga  acgcggtgag  gctggtattc  caggtgttcc
aggagctaaa  ggcgaagatg  gcaaggatgg  atcacctgga  gaacctggtg
caaatgggct  tccaggagct  gcaggagaaa  ggggtgcccc  tgggttccga
ggacctgctg  gaccaaatgg  catcccagga  gaaaagggtc  ctgctggaga
gcgtggtgct  ccaggccctg  cagggcccag  aggagctgct  ggagaacctg
gcagagatgg  cgtccctgga  ggtccaggaa  tgagggcat   gcccggaagt
ccaggaggac  caggaagtga  tgggaaacca  gggcctcccg  gaagtcaagg
agaaagtggt  cgaccaggtc  ctcctgggcc  atctggtccc  cgaggtcagc
ctggtgtcat  gggcttcccc  ggtcctaaag  gaaatgatgg  tgctcctggt
```

FIG. 8

```
aagaatggag aacgaggtgg ccctggagga cctggccctc agggtcctcc
tggaaagaat ggtgaaactg gacctcaagg accccaggg cctactgggc
ctggtggtga caaaggagac acaggacccc ctggtccaca aggattacaa
ggcttgcctg gtacaggtgg tcctccagga gaaatggaa aacctggga
accaggtcca aagggtgatg ccggtgcacc tggagctcca ggaggcaagg
gtgatgctgg tgcccctggt gaacgtggac ctcctggatt ggcaggggcc
ccaggactta gaggtggagc tggtccccct ggtcccgaag gaggaaaggg
tgctgctggt cctcctgggc cacctggtgc tgctggtact cctggtctgc
aaggaatgcc tggagaaaga ggaggtcttg gaagtcctgg tccaaagggt
gacaagggtg aaccaggcgg cccaggtgct gatggtgtcc cagggaaaga
tggcccaagg ggtcctactg gtcctattgg tcctcctggc ccagctggcc
agcctggaga taagggtgaa ggtggtgccc ccggacttcc aggtatagct
ggacctcgtg gtagccctgg tgagagaggt gaaactggcc ctccaggacc
tgctggtttc cctggtgctc ctggacagaa tggtgaacct ggtggtaaag
gagaaagagg ggctccgggt gagaaggtg aaggaggccc tcctggagtt
gcaggacccc ctggaggttc tggacctgct ggtcctcctg gtccccaagg
tgtcaaaggt gaacgtggca gtcctggtgg acctggtgct gctggcttcc
ctggtgctcg tggtcttcct ggtcctcctg gtagtaatgg taacccagga
cccccaggtc ccagcggttc tccaggcaag gatgggcccc caggtcctgc
gggtaacact ggtgctcctg gcagccctgg agtgtctgga ccaaaaggtg
atgctggcca accaggagag aagggatcgc ctggtgccca gggcccacca
ggagctccag gcccacttgg gattgctggg atcactggag cacggggtct
tgcaggacca ccaggcatgc caggtcctag gggaagccct ggccctcagg
gtgtcaaggg tgaaagtggg aaaccaggag ctaacggtct cagtggagaa
cgtggtcccc ctggacccca gggtcttcct ggtctggctg gtacagctgg
tgaacctgga agagatggaa accctggatc agatggtctt ccaggccgag
atggatctcc tggtggcaag ggtgatcgtg gtgaaaatgg ctctcctggt
gcccctggcg ctcctggtca tccaggccca cctggtcctg tcggtccagc
tggaaagagt ggtgacagag gagaaagtgg ccctgctggc cctgctggtg
ctcccggtcc tgctggttcc cgaggtgctc ctggtcctca aggcccacgt
ggtgacaaag gtgaaacagg tgaacgtgga gctgctggca tcaaaggaca
tcgaggattc cctggtaatc caggtgcccc aggttctcca ggccctgctg
gtcagcaggg tgcaatcggc agtccaggac ctgcaggccc cagaggacct
gttggaccca gtggacctcc tggcaaagat ggaccagtg gacatccagg
tcccattgga ccaccagggc ctcgaggtaa cagaggtgaa agaggatctg
agggctcccc aggccaccca gggcaaccag gccctcctgg acctcctggt
gcccctggtc cttgctgtgg tggtgttgga gccgctgcca ttgctgggat
tggaggtgaa aaagctggcg gttttgcccc gtattatgga gatgaaccaa
tggatttcaa aatcaacacc gatgagatta tgacttcact caagtctgtt
aatggacaaa tagaaagcct cattagtcct gatggttctc gtaaaaaccc
cgctagaaac tgcagagacc tgaaattctg ccatcctgaa ctcaagagtg
gagaatactg ggttgaccct aaccaaggat gcaaattgga tgctatcaag
gtattctgta atatggaaac tgggaaaca tgcataagtg ccaatccttt
gaatgttcca cggaaacact ggtggacaga ttctagtgct gagaagaaac
acgtttggtt tggagagtcc atggatggtg gttttcagtt tagctacggc
aatcctgaac ttcctgaaga tgtccttgat gtgcagctgg cattccttcg
acttctctcc agccgagctt cccagaacat cacatatcac tgcaaaaata
gcattgcata catggatcag gccagtggaa atgtaaagaa ggcctgaag
ctgatggggt caaatgaagg tgaattcaag gctgaaggaa atagcaaatt
```

FIG. 8 cont;

```
cacctacaca gttctggagg atggttgcac gaaacacact ggggaatgga
gcaaaacagt ctttgaatat cgaacacgca aggctgtgag actacctatt
gtagatattg caccctatga cattggtggt cctgatcaag aatttggtgt
ggacgttggc cctgtttgct ttttataa
```

FIG. 8 cont;

```
Met K S S G L F P F L V L L A L G T L A P W A V E G S G K S
F K A G V C P P K K S A Q C L R Y K K P E C Q S D W Q C P G
K K R C C P D T C G I K C L D P V D T P N P T R R K P G K C
P V T Y G Q C L Met L N P P N F C E Met D G Q C K R D L K C
C Met G Met C G K S C V S P V K A

A V E G G C S H L G Q S Y A D R D V W K P E P C Q I C V C D
S G S V L C D D I I C D D Q E L D C P N P E I P F G E C C A
V C P Q P P T A P T R P P N G Q G P Q G P K G D P G P P G I
P G R N G D P G I P G Q P G S P G S P G P P G I C E S C P T
G P Q N Y S P Q Y D S Y D V K S G V A V G G L A G Y P G P A
G P P G P P G P P G T S G H P G S P G S P G Y Q G P P G E P
G Q A G P S G P P G P P G A I G P S G P A G K D G E S G R P
G R P G E R G L P G P P G I K G P A G I P G F P G Met K G H
R G F D G R N G E K G E T G A P G L K G E N G L P G E N G A
P G P Met G P R G A P G E R G R P G L P G A A G A R G N D G
A R G S D G Q P G P P G P P G T A G F P G S P G A K G E V G
P A G S P G S N G A P G Q R G E P G P Q G H A G A Q G P P G
P P G I N G S P G G K G E Met G P A G I P G A P G L Met G A
R G P P G P A G A N G A P G L R G G A G E P G K N G A K G E
P G P R G E R G E A G I P G V P G A K G E D G K D G S P G E
P G A N G L P G A A G E R G A P G F R G P A G P N G I P G E
K G P A G E R G A P G P A G P R G A A G E P G R D G V P G G
P G Met R G Met P G S P G G P G S D G K P G P P G S Q G E S
G R P G P P G P S G P R G Q P G V Met G F P G P K G N D G A
P G K N G E R G G P G G P G P Q G P P G K N G E T G P Q G P
P G P T G P G G D K G D T G P P G P Q G L Q G L P G T G G P
P G E N G K P G E P G P K G D A G A P G A P G G K G D A G A
P G E R G P P G L A G A P G L R G G A G P P G P E G G K G A
A G P P G P P G A A G T P G L Q G Met P G E R G G L G S P G
P K G D K G E P G G P G A D G V P G K D G P R G P T G P I G
P P G P A G Q P G D K G E G G A P G L P G I A G P R G S P G
E R G E T G P P G P A G F P G A P G Q N G E P G G K G E R G
A P G E K G E G G P P G V A G P P G G S G P A G P P G P Q G
V K G E R G S P G G P G A A G F P G A R G L P G P P G S N G
N P G P P G P S G S P G K D G P P G P A G N T A P G S P G
V S G P K G D A G Q P G E K G S P G A Q G P P G A P G P L G
I A G I T G A R G L A G P P G Met P G P R G S P G P Q G V K
G E S G K P G A N G L S G E R G P P G P Q G L P G L A G T A
G E P G R D G N P G S D G L P G R D G S P G G K G D R G E N
G S P G A P G A P G H P G P P G P V G P A G K S G D R G E S
```

FIG. 9

```
G P A G P A G A P G P A G S R G A P G P Q G P R G D K G E T
G E R G A A G I K G H R G F P G N P G A P G S P G P A G Q Q
G A I G S P G P A G P R G P V G P S G P P G K D G T S G H P
G P I G P P G P R G N R G E R G S E G S P G H P G Q P G P P
G P P G A P G P C C G G V G A A A I A G I G G E K A G G F A
P Y Y G D E P Met D F K I N T D E I Met T S L K S V N G Q I
E S L I S P D G S R K N P A R N C R D L K F C H P E L K S G
E Y W V D P N Q G C K L D A I K V F C N Met E T G E T C I S
A N P L N V P R K H W W T D S S A E K K H V W F G E S Met D
G G F Q F S Y G N P E L P E D V L D V Q L A F L R L L S S R
A S Q N I T Y H C K N S I A Y Met D Q A S G N V K K A L K L
Met G S N E G E F K A E G N S K F T Y T V L E D G C T K H T
G E W S K T V F E Y R T R K A V R L P I V D I A P Y D I G G
P D Q E F G V D V G P V C F L Stop
```

FIG. 9 cont;

SEQUENCE LISTING

```
<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide for PCR

<400> SEQUENCE: 1
aattaaccct cactaaaggg                                           20

<210> SEQ ID NO 2
<211> LENGTH: 31
<212> TYPE: DNA
<213> ORGANISM: Artificial Sequence
<220> FEATURE:
<223> OTHER INFORMATION: Oligonucleotide for PCR

<400> SEQUENCE: 2
acagagatgt tgccaaaata atagtgggat g                              31

<210> SEQ ID NO 3
<211> LENGTH: 31
<212> TYPE: DNA
<213> ORGANISM: Artificial Sequence
<220> FEATURE:
<223> OTHER INFORMATION: Oligonucleotide for PCR

<400> SEQUENCE: 3
tattttggca acatctctgt ccttgtttct c                              31

<210> SEQ ID NO 4
<211> LENGTH: 31
<212> TYPE: DNA
<213> ORGANISM: Artificial Sequence
<220> FEATURE:
```

-continued

```
<223> OTHER INFORMATION: Oligonucleotide for PCR

<400> SEQUENCE: 4
cttgaccatt agcatcttgc cacaccttca c                                31

<210> SEQ ID NO 5
<211> LENGTH: 31
<212> TYPE: DNA
<213> ORGANISM: Artificial Sequence
<220> FEATURE:
<223> OTHER INFORMATION: Oligonucleotide for PCR

<400> SEQUENCE: 5
gcaagatgct aatggtcaag gacctcaagg c                                31

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide for PCR

<400> SEQUENCE: 6
agaccctgca ggtccaactt                                             20

<210> SEQ ID NO 7
<211> LENGTH: 32
<212> TYPE: DNA
<213> ORGANISM: Artificial Sequence
<220> FEATURE:
<223> OTHER INFORMATION: Oligonucleotide for PCR

<400> SEQUENCE: 7
gttgtaaaac ggcggccgct gaattgtaat ac                               32

<210> SEQ ID NO 8
<211> LENGTH: 32
<212> TYPE: DNA
<213> ORGANISM: Artificial Sequence
<220> FEATURE:
<223> OTHER INFORMATION: Oligonucleotide for PCR

<400> SEQUENCE: 8
gtattacaat tcagcggccg ccgttttaca ac                               32

<210> SEQ ID NO 9
<211> LENGTH: 5853
<212> TYPE: DNA
<213> ORGANISM: Artificial Sequence
<220> FEATURE:
<223> OTHER INFORMATION: DNA molecule based on procollagen type III
      N-propeptide. Sequence prior to N100 replaced with the sequence
      for the G123 domains of the alpha3 chain of laminin-5 whilst
      retaining the collagen III signal sequence.

<400> SEQUENCE: 9
atgatgagct ttgtgcaaaa ggggagctgg ctacttctcg ctctgcttca tcccactatt    60
attttggcaa catctctgtc cttgtttctc caaaggccca actcaagaga aaatggggt    120 actgagaata tgtttgtgat gtaccttgga aataaagatg cctcccggga ctacatcggc   180
atggcagttg tggatggcca gctcacctgt gtctacaacc tggggaccg tgaggctgaa   240 ctccaagtgg accagatctt gaccaagagt gagactaagg aggcagttat ggatcgggtg   300
aaatttcaga gaatttatca gtttgcaagg cttaattaca ccaaaggagc cacatccagt   360
```

-continued

```
aaaccagaaa cacccggagt ctatgacatg gatggtagaa atagcaatac actccttaat    420
ttggatcctg aaaatgttgt attttatgtt ggaggttacc cacctgattt taaacttccc    480
agtcgactaa gtttccctcc atacaaaggt tgtattgaat tagatgacct caatgaaaat    540
gttctgagct tgtacaactt caaaaaaaca ttcaatctca acacaactga agtggagcct    600
tgtagaagga ggaaggaaga gtcagacaaa aattattttg aaggtacggg ctatgctcga    660
gttccaactc aaccacatgc tcccatccca acctttggac agacaattca gaccaccgtg    720
gatagaggct tgctgttctt tgcagaaaac ggggatcgct tcatatctct aaatatagaa    780
gatggcaagc tcatggtgag atacaaactg aattcagagc taccaaaaga gagaggagtt    840
ggagacgcca taaacaacgg cagagaccat tcgattcaga tcaaaattgg aaaactccaa    900
aagcgtatgt ggataaatgt ggacgttcaa aacactataa ttgatggtga agtatttgat    960
ttcagcacat attatctggg aggaattcca attgcaatca gggaaagatt taacatttct   1020
acgcctgctt tccgaggctg catgaaaaat ttgaagaaaa ccagtggtgt cgttagattg   1080
aatgatactg tgggagtaac caaaaagtgc tcggaagact ggaagcttgt gcgatctgcc   1140
tcattctcca gaggaggaca attgagtttc actgatttgg gcttaccacc tactgaccac   1200
ctccaggcct catttggatt tcagaccttt caacccagtg gcatattatt agatcatcag   1260
acatggacaa ggaacctgca ggtcactctg aagatggtt acattgaatt gagcaccagc   1320
gatagcggcg gcccaatttt taaatctcca cagacgtata tggatggttt actgcattat   1380
gtatctgtaa taagcgacaa ctctggacta cggcttctca tcgatgacca gcttctgaga   1440
aatagcaaaa ggctaaaaca catttcaagt tcccggcagt ctctgcgtct gggcgggagc   1500
aattttgagg gttgtattag caatgttttt gtccagaggt tatcactgag tcctgaagtc   1560
ctagatttga ccagtaactc tctcaagaga gatgtgtccc tgggaggctg cagtttaaac   1620
aaaccacctt ttctaatgtt gcttaaaggt tctaccaggt ttaacaagac caagactttt   1680
cgtatcaacc agctgttgca ggacacacca gtggcctccc caaggagcgt gaaggtgtgg   1740
caagatgcta atggtcaagg acctcaaggc cccaagggag atccaggccc tcctggtatt   1800
cctgggagaa atggtgaccc tggtattcca ggacaaccag ggtcccctgg ttctcctggc   1860
cccccctggaa tctgtgaatc atgccctact ggtcctcaga actattctcc ccagtatgat   1920
tcatatgatg tcaagtctgg agtagcagta ggaggactcg caggctatcc tggaccagct   1980
ggccccccag ccctcccggg tccccctggt acatctggtc atcctggttc ccctggatct   2040
ccaggatacc aaggaccccc tggtgaacct gggcaagctg gtccttcagg ccctccagga   2100
cctcctggtg ctataggtcc atctggtcct gctggaaaag atggagaatc aggtagaccc   2160
ggacgacctg gagagcgagg attgcctgga cctccaggta tcaaaggtcc agctgggata   2220
cctggattcc ctggtatgaa aggacacaga ggcttcgatg gacgaaatgg agaaaagggt   2280
gaaacaggtg ctcctggatt aaagggtgaa aatggtcttc caggcgaaaa tggagctcct   2340
ggacccatgg gtccaagagg ggctcctggt gagcgaggac ggccaggact tcctggggct   2400
gcaggtgctc ggggtaatga cggtgctcga ggcagtgatg gtcaaccagg ccctcctggt   2460
cctcctggaa ctgccggatt ccctggatcc cctggtgcta agggtgaagt ggacctgca    2520
gggtctcctg gttcaaatgg tgcccctgga caaagaggag aacctggacc tcagggacac   2580
gctggtgctc aaggtcctcc tggccctcct gggattaatg gtagtcctgg tggtaaaggc   2640
gaaatgggtc ccgctggcat tcctggagct cctggactga tgggagcccg gggtcctcca   2700
ggaccagccg gtgctaatgg tgctcctgga ctgcgaggtg gtgcaggtga gcctggtaag   2760
```

```
aatggtgcca aaggagagcc cggaccacgt ggtgaacgcg gtgaggctgg tattccaggt    2820
gttccaggag ctaaaggcga agatggcaag gatggatcac ctggagaacc tggtgcaaat    2880
gggcttccag gagctgcagg agaaaggggg gcccctgggt tccgaggacc tgctggacca    2940
aatggcatcc caggagaaaa gggtcctgct ggagagcgtg gtgctccagg ccctgcaggg    3000
cccagaggag ctgctggaga acctggcaga gatggcgtcc ctggaggtcc aggaatgagg    3060
ggcatgcccg gaagtccagg aggaccagga agtgatggga aaccagggcc tcccggaagt    3120
caaggagaaa gtggtcgacc aggtcctcct gggccatctg gtccccgagg tcagcctggt    3180
gtcatgggct tccccggtcc taaaggaaat gatggtgctc ctggtaagaa tggagaacga    3240
ggtggccctg gaggacctgg ccctcagggt cctcctggaa agaatggtga aactggacct    3300
caaggacccc cagggcctac tgggcctggt ggtgacaaag agacacagg accccctggt     3360 ccacaaggat tacaaggctt gcctggtaca ggtggtcctc caggagaaaa tggaaaacct    3420
ggggaaccag gtccaaaggg tgatgccggt gcacctggag ctccaggagg caagggtgat    3480
gctggtgccc ctggtgaacg tggacctcct ggattggcag gggccccagg acttagaggt    3540
ggagctggtc ccctggtcc cgaaggagga aagggtgctg ctggtcctcc tgggccacct     3600
ggtgctgctg gtactcctgg tctgcaagga atgcctggag aaagaggagg tcttggaagt    3660
cctggtccaa agggtgacaa gggtgaacca ggcggcccag gtgctgatgg tgtcccaggg    3720
aaagatggcc caaggggtcc tactggtcct attggtcctc ctggcccagc tggccagcct    3780
ggagataagg gtgaaggtgg tgcccccgga cttccaggta tagctggacc tcgtggtagc    3840
cctggtgaga gaggtgaaac tggccctcca ggacctgctg gtttccctgg tgctcctgga    3900
cagaatggtg aacctggtgg taaaggagaa agaggggctc cgggtgagaa aggtgaagga    3960
ggccctcctg gagttgcagg acccctggaa ggttctggac ctgctggtcc tcctggtccc    4020
caaggtgtca aaggtgaacg tggcagtcct ggtggacctg gtgctgctgg cttccctggt    4080
gctcgtggtc ttcctggtcc tctggtagt aatggtaacc caggaccccc aggtccagc     4140 ggttctccag gcaaggatgg gccccaggt cctgcgggta acactggtgc tcctggcagc    4200
cctggagtgt ctggaccaaa aggtgatgct ggccaaccag gagagaaggg atcgcctggt    4260
gcccagggcc caccaggagc tccaggccca cttgggattg ctgggatcac tggagcacgg    4320
ggtcttgcag gaccaccagg catgccaggt cctaggggaa gccctggccc tcagggtgtc    4380
aagggtgaaa gtgggaaacc aggagctaac ggtctcagtg gagaacgtgg tccccctgga    4440
ccccagggtc ttcctggtct ggctggtaca gctggtgaac ctggaagaga tggaaaccct    4500
ggatcagatg gtcttccagg ccgagatgga tctcctggtg gcaagggtga tcgtggtgaa    4560
aatggctctc ctggtgcccc tggcgctcct ggtcatccag gcccacctgg tcctgtcggt    4620
ccagctggaa agagtggtga cagaggagaa agtggccctg ctggccctgc tggtgctccc    4680
ggtcctgctg gttcccgagg tgctcctggt cctcaaggcc cacgtggtga caaaggtgaa    4740
acaggtgaac gtggagctgc tggcatcaaa ggacatcgag gattccctgg taatccaggt    4800
gccccaggtt ctccaggccc tgctggtcag cagggtgcaa tcggcagtcc aggacctgca    4860
ggccccagag gacctgttgg acccagtgga cctcctggca agatggaac cagtggacat    4920 ccaggtccca ttgaccacc agggcctcga ggtaacagag gtgaaagagg atctgagggc    4980
tccccaggcc acccagggca accaggccct cctggacctc ctggtgcccc tggtcccttgc   5040 tgtggtggtg ttgagccgc tgccattgct gggattggag gtgaaaaagc tggcggtttt    5100
```

-continued

```
gccccgtatt atgagatga accaatggat ttcaaaatca acaccgatga gattatgact    5160
tcactcaagt ctgttaatgg acaaatagaa agcctcatta gtcctgatgg ttctcgtaaa   5220
aaccccgcta gaaactgcag agacctgaaa ttctgccatc ctgaactcaa gagtggagaa   5280
tactgggttg accctaacca aggatgcaaa ttggatgcta tcaaggtatt ctgtaatatg   5340
gaaactgggg aaacatgcat aagtgccaat cctttgaatg ttccacggaa acactggtgg   5400
acagattcta gtgctgagaa gaaacacgtt tggtttggag agtccatgga tggtggtttt   5460
cagtttagct acggcaatcc tgaacttcct gaagatgtcc ttgatgtgca gctggcattc   5520
cttcgacttc tctccagccg agcttcccag aacatcacat atcactgcaa aaatagcatt   5580
gcatacatgg atcaggccag tggaaatgta aagaaggccc tgaagctgat ggggtcaaat   5640
gaaggtgaat tcaaggctga aggaaatagc aaattcacct acacagttct ggaggatggt   5700
tgcacgaaac acactgggga atggagcaaa acagtctttg aatatcgaac acgcaaggct   5760
gtgagactac ctattgtaga tattgcaccc tatgacattg gtggtcctga tcaagaattt   5820
ggtgtggacg ttggccctgt ttgcttttta taa                                5853
```

<210> SEQ ID NO 10
<211> LENGTH: 1950
<212> TYPE: PRT
<213> ORGANISM: Artificial Sequence
<220> FEATURE:
<223> OTHER INFORMATION: Sequence of the modified pro-alpha chain

<400> SEQUENCE: 10

```
Met Met Ser Phe Val Gln Lys Gly Ser Trp Leu Leu Leu Ala Leu Leu
  1               5                  10                  15

His Pro Thr Ile Ile Leu Ala Thr Ser Leu Ser Leu Phe Leu Gln Arg
             20                  25                  30

Pro Asn Ser Arg Glu Asn Gly Gly Thr Glu Asn Met Phe Val Met Tyr
         35                  40                  45

Leu Gly Asn Lys Asp Ala Ser Arg Asp Tyr Ile Gly Met Ala Val Val
     50                  55                  60

Asp Gly Gln Leu Thr Cys Val Tyr Asn Leu Gly Asp Arg Glu Ala Glu
 65                  70                  75                  80

Leu Gln Val Asp Gln Ile Leu Thr Lys Ser Glu Thr Lys Glu Ala Val
                 85                  90                  95

Met Asp Arg Val Lys Phe Gln Arg Ile Tyr Gln Phe Ala Arg Leu Asn
            100                 105                 110

Tyr Thr Lys Gly Ala Thr Ser Ser Lys Pro Glu Thr Pro Gly Val Tyr
        115                 120                 125

Asp Met Asp Gly Arg Asn Ser Asn Thr Leu Leu Asn Leu Asp Pro Glu
    130                 135                 140

Asn Val Val Phe Tyr Val Gly Gly Tyr Pro Pro Asp Phe Lys Leu Pro
145                 150                 155                 160

Ser Arg Leu Ser Phe Pro Pro Tyr Lys Gly Cys Ile Glu Leu Asp Asp
                165                 170                 175

Leu Asn Glu Asn Val Leu Ser Leu Tyr Asn Phe Lys Lys Thr Phe Asn
            180                 185                 190

Leu Asn Thr Thr Glu Val Glu Pro Cys Arg Arg Arg Lys Glu Glu Ser
        195                 200                 205

Asp Lys Asn Tyr Phe Glu Gly Thr Gly Tyr Ala Arg Val Pro Thr Gln
    210                 215                 220

Pro His Ala Pro Ile Pro Thr Phe Gly Gln Thr Ile Gln Thr Thr Val
```

-continued

```
            225                 230                 235                 240
Asp Arg Gly Leu Leu Phe Phe Ala Glu Asn Gly Asp Arg Phe Ile Ser
                245                 250                 255
Leu Asn Ile Glu Asp Gly Lys Leu Met Val Arg Tyr Lys Leu Asn Ser
                260                 265                 270
Glu Leu Pro Lys Glu Arg Gly Val Gly Asp Ala Ile Asn Asn Gly Arg
                275                 280                 285
Asp His Ser Ile Gln Ile Lys Ile Gly Lys Leu Gln Lys Arg Met Trp
                290                 295                 300
Ile Asn Val Asp Val Gln Asn Thr Ile Ile Asp Gly Glu Val Phe Asp
305                 310                 315                 320
Phe Ser Thr Tyr Tyr Leu Gly Gly Ile Pro Ile Ala Ile Arg Glu Arg
                325                 330                 335
Phe Asn Ile Ser Thr Pro Ala Phe Arg Gly Cys Met Lys Asn Leu Lys
                340                 345                 350
Lys Thr Ser Gly Val Val Arg Leu Asn Asp Thr Val Gly Val Thr Lys
                355                 360                 365
Lys Cys Ser Glu Asp Trp Lys Leu Val Arg Ser Ala Ser Phe Ser Arg
                370                 375                 380
Gly Gly Gln Leu Ser Phe Thr Asp Leu Gly Leu Pro Pro Thr Asp His
385                 390                 395                 400
Leu Gln Ala Ser Phe Gly Phe Gln Thr Phe Gln Pro Ser Gly Ile Leu
                405                 410                 415
Leu Asp His Gln Thr Trp Thr Arg Asn Leu Gln Val Thr Leu Glu Asp
                420                 425                 430
Gly Tyr Ile Glu Leu Ser Thr Ser Asp Ser Gly Gly Pro Ile Phe Lys
                435                 440                 445
Ser Pro Gln Thr Tyr Met Asp Gly Leu Leu His Tyr Val Ser Val Ile
                450                 455                 460
Ser Asp Asn Ser Gly Leu Arg Leu Leu Ile Asp Gln Leu Leu Arg
465                 470                 475                 480
Asn Ser Lys Arg Leu Lys His Ile Ser Ser Arg Gln Ser Leu Arg
                485                 490                 495
Leu Gly Gly Ser Asn Phe Glu Gly Cys Ile Ser Asn Val Phe Val Gln
                500                 505                 510
Arg Leu Ser Leu Ser Pro Glu Val Leu Asp Leu Thr Ser Asn Ser Leu
                515                 520                 525
Lys Arg Asp Val Ser Leu Gly Gly Cys Ser Leu Asn Lys Pro Pro Phe
                530                 535                 540
Leu Met Leu Leu Lys Gly Ser Thr Arg Phe Asn Lys Thr Lys Thr Phe
545                 550                 555                 560
Arg Ile Asn Gln Leu Leu Gln Asp Thr Pro Val Ala Ser Pro Arg Ser
                565                 570                 575
Val Lys Val Trp Gln Asp Ala Asn Gln Gly Pro Gln Gly Pro Lys
                580                 585                 590
Gly Asp Pro Gly Pro Pro Gly Ile Pro Gly Arg Asn Gly Asp Pro Gly
                595                 600                 605
Ile Pro Gly Gln Pro Gly Ser Pro Gly Ser Pro Gly Pro Gly Ile
                610                 615                 620
Cys Glu Ser Cys Pro Thr Gly Pro Gln Asn Tyr Ser Pro Gln Tyr Asp
625                 630                 635                 640
Ser Tyr Asp Val Lys Ser Gly Val Ala Val Gly Gly Leu Ala Gly Tyr
                645                 650                 655
```

-continued

```
Pro Gly Pro Ala Gly Pro Pro Gly Pro Pro Gly Pro Pro Gly Thr Ser
            660                 665                 670
Gly His Pro Gly Ser Pro Gly Ser Pro Gly Tyr Gln Gly Pro Pro Gly
            675                 680                 685
Glu Pro Gly Gln Ala Gly Pro Ser Gly Pro Pro Gly Pro Pro Gly Ala
            690                 695                 700
Ile Gly Pro Ser Gly Pro Ala Gly Lys Asp Gly Glu Ser Gly Arg Pro
705                 710                 715                 720
Gly Arg Pro Gly Glu Arg Gly Leu Pro Gly Pro Pro Gly Ile Lys Gly
                725                 730                 735
Pro Ala Gly Ile Pro Gly Phe Pro Gly Met Lys Gly His Arg Gly Phe
            740                 745                 750
Asp Gly Arg Asn Gly Glu Lys Gly Glu Thr Gly Ala Pro Gly Leu Lys
            755                 760                 765
Gly Glu Asn Gly Leu Pro Gly Glu Asn Gly Ala Pro Gly Pro Met Gly
            770                 775                 780
Pro Arg Gly Ala Pro Gly Glu Arg Gly Arg Pro Gly Leu Pro Gly Ala
785                 790                 795                 800
Ala Gly Ala Arg Gly Asn Asp Gly Ala Arg Gly Ser Asp Gly Gln Pro
                805                 810                 815
Gly Pro Pro Gly Pro Pro Gly Thr Ala Gly Phe Pro Gly Ser Pro Gly
            820                 825                 830
Ala Lys Gly Glu Val Gly Pro Ala Gly Ser Pro Gly Ser Asn Gly Ala
            835                 840                 845
Pro Gly Gln Arg Gly Glu Pro Gly Pro Gln Gly His Ala Gly Ala Gln
            850                 855                 860
Gly Pro Pro Gly Pro Pro Gly Ile Asn Gly Ser Pro Gly Gly Lys Gly
865                 870                 875                 880
Glu Met Gly Pro Ala Gly Ile Pro Gly Ala Pro Gly Leu Met Gly Ala
                885                 890                 895
Arg Gly Pro Pro Gly Pro Ala Gly Ala Asn Gly Ala Pro Gly Leu Arg
            900                 905                 910
Gly Gly Ala Gly Glu Pro Gly Lys Asn Gly Ala Lys Gly Glu Pro Gly
            915                 920                 925
Pro Arg Gly Glu Arg Gly Glu Ala Gly Ile Pro Gly Val Pro Gly Ala
            930                 935                 940
Lys Gly Glu Asp Gly Lys Asp Gly Ser Pro Gly Glu Pro Gly Ala Asn
945                 950                 955                 960
Gly Leu Pro Gly Ala Ala Gly Glu Arg Gly Ala Pro Gly Phe Arg Gly
                965                 970                 975
Pro Ala Gly Pro Asn Gly Ile Pro Gly Glu Lys Gly Pro Ala Gly Glu
            980                 985                 990
Arg Gly Ala Pro Gly Pro Ala Gly Pro Arg Gly Ala Ala Gly Glu Pro
            995                1000                1005
Gly Arg Asp Gly Val Pro Gly Gly Pro Gly Met Arg Gly Met Pro
            1010                1015                1020
Gly Ser Pro Gly Gly Pro Gly Ser Asp Gly Lys Pro Gly Pro Pro
            1025                1030                1035
Gly Ser Gln Gly Glu Ser Gly Arg Pro Gly Pro Pro Gly Pro Ser
            1040                1045                1050
Gly Pro Arg Gly Gln Pro Gly Val Met Gly Phe Pro Gly Pro Lys
            1055                1060                1065
```

-continued

```
Gly Asn Asp Gly Ala Pro Gly Lys Asn Gly Glu Arg Gly Gly Pro
    1070                1075                1080

Gly Gly Pro Gly Pro Gln Gly Pro Pro Gly Lys Asn Gly Glu Thr
    1085                1090                1095

Gly Pro Gln Gly Pro Pro Gly Pro Thr Gly Pro Gly Gly Asp Lys
    1100                1105                1110

Gly Asp Thr Gly Pro Pro Gly Pro Gln Gly Leu Gln Gly Leu Pro
    1115                1120                1125

Gly Thr Gly Gly Pro Pro Gly Glu Asn Gly Lys Pro Gly Glu Pro
    1130                1135                1140

Gly Pro Lys Gly Asp Ala Gly Ala Pro Gly Ala Pro Gly Gly Lys
    1145                1150                1155

Gly Asp Ala Gly Ala Pro Gly Glu Arg Gly Pro Pro Gly Leu Ala
    1160                1165                1170

Gly Ala Pro Gly Leu Arg Gly Gly Ala Gly Pro Pro Gly Pro Glu
    1175                1180                1185

Gly Gly Lys Gly Ala Ala Gly Pro Pro Gly Pro Pro Gly Ala Ala
    1190                1195                1200

Gly Thr Pro Gly Leu Gln Gly Met Pro Gly Glu Arg Gly Gly Leu
    1205                1210                1215

Gly Ser Pro Gly Pro Lys Gly Asp Lys Gly Glu Pro Gly Gly Pro
    1220                1225                1230

Gly Ala Asp Gly Val Pro Gly Lys Asp Gly Pro Arg Gly Pro Thr
    1235                1240                1245

Gly Pro Ile Gly Pro Pro Gly Pro Ala Gly Gln Pro Gly Asp Lys
    1250                1255                1260

Gly Glu Gly Gly Ala Pro Gly Leu Pro Gly Ile Ala Gly Pro Arg
    1265                1270                1275

Gly Ser Pro Gly Glu Arg Gly Glu Thr Gly Pro Pro Gly Pro Ala
    1280                1285                1290

Gly Phe Pro Gly Ala Pro Gly Gln Asn Gly Glu Pro Gly Gly Lys
    1295                1300                1305

Gly Glu Arg Gly Ala Pro Gly Glu Lys Gly Glu Gly Gly Pro Pro
    1310                1315                1320

Gly Val Ala Gly Pro Pro Gly Gly Ser Gly Pro Ala Gly Pro Pro
    1325                1330                1335

Gly Pro Gln Gly Val Lys Gly Glu Arg Gly Ser Pro Gly Gly Pro
    1340                1345                1350

Gly Ala Ala Gly Phe Pro Gly Ala Arg Gly Leu Pro Gly Pro Pro
    1355                1360                1365

Gly Ser Asn Gly Asn Pro Gly Pro Pro Gly Pro Ser Gly Ser Pro
    1370                1375                1380

Gly Lys Asp Gly Pro Pro Gly Pro Ala Gly Asn Thr Gly Ala Pro
    1385                1390                1395

Gly Ser Pro Gly Val Ser Gly Pro Lys Gly Asp Ala Gly Gln Pro
    1400                1405                1410

Gly Glu Lys Gly Ser Pro Gly Ala Gln Gly Pro Pro Gly Ala Pro
    1415                1420                1425

Gly Pro Leu Gly Ile Ala Gly Ile Thr Gly Ala Arg Gly Leu Ala
    1430                1435                1440

Gly Pro Pro Gly Met Pro Gly Pro Arg Gly Ser Pro Gly Pro Gln
    1445                1450                1455

Gly Val Lys Gly Glu Ser Gly Lys Pro Gly Ala Asn Gly Leu Ser
```

```
                          1460                1465                1470

Gly Glu Arg Gly Pro Pro Gly Pro Gln Gly Leu Pro Gly Leu Ala
    1475                1480                1485

Gly Thr Ala Gly Glu Pro Gly Arg Asp Gly Asn Pro Gly Ser Asp
    1490                1495                1500

Gly Leu Pro Gly Arg Asp Gly Ser Pro Gly Lys Gly Asp Arg
    1505                1510                1515

Gly Glu Asn Gly Ser Pro Gly Ala Pro Gly Ala Pro Gly His Pro
    1520                1525                1530

Gly Pro Pro Gly Pro Val Gly Pro Ala Gly Lys Ser Gly Asp Arg
    1535                1540                1545

Gly Glu Ser Gly Pro Ala Gly Pro Ala Gly Ala Pro Gly Pro Ala
    1550                1555                1560

Gly Ser Arg Gly Ala Pro Gly Pro Gln Gly Pro Arg Gly Asp Lys
    1565                1570                1575

Gly Glu Thr Gly Glu Arg Gly Ala Ala Gly Ile Lys Gly His Arg
    1580                1585                1590

Gly Phe Pro Gly Asn Pro Gly Ala Pro Gly Ser Pro Gly Pro Ala
    1595                1600                1605

Gly Gln Gln Gly Ala Ile Gly Ser Pro Gly Pro Ala Gly Pro Arg
    1610                1615                1620

Gly Pro Val Gly Pro Ser Gly Pro Pro Gly Lys Asp Gly Thr Ser
    1625                1630                1635

Gly His Pro Gly Pro Ile Gly Pro Pro Gly Pro Arg Gly Asn Arg
    1640                1645                1650

Gly Glu Arg Gly Ser Glu Gly Ser Pro Gly His Pro Gly Gln Pro
    1655                1660                1665

Gly Pro Pro Gly Pro Pro Gly Ala Pro Gly Pro Cys Cys Gly Gly
    1670                1675                1680

Val Gly Ala Ala Ala Ile Ala Gly Ile Gly Gly Glu Lys Ala Gly
    1685                1690                1695

Gly Phe Ala Pro Tyr Tyr Gly Asp Glu Pro Met Asp Phe Lys Ile
    1700                1705                1710

Asn Thr Asp Glu Ile Met Thr Ser Leu Lys Ser Val Asn Gly Gln
    1715                1720                1725

Ile Glu Ser Leu Ile Ser Pro Asp Gly Ser Arg Lys Asn Pro Ala
    1730                1735                1740

Arg Asn Cys Arg Asp Leu Lys Phe Cys His Pro Glu Leu Lys Ser
    1745                1750                1755

Gly Glu Tyr Trp Val Asp Pro Asn Gln Gly Cys Lys Leu Asp Ala
    1760                1765                1770

Ile Lys Val Phe Cys Asn Met Glu Thr Gly Glu Thr Cys Ile Ser
    1775                1780                1785

Ala Asn Pro Leu Asn Val Pro Arg Lys His Trp Trp Thr Asp Ser
    1790                1795                1800

Ser Ala Glu Lys Lys His Val Trp Phe Gly Glu Ser Met Asp Gly
    1805                1810                1815

Gly Phe Gln Phe Ser Tyr Gly Asn Pro Glu Leu Pro Glu Asp Val
    1820                1825                1830

Leu Asp Val Gln Leu Ala Phe Leu Arg Leu Leu Ser Ser Arg Ala
    1835                1840                1845

Ser Gln Asn Ile Thr Tyr His Cys Lys Asn Ser Ile Ala Tyr Met
    1850                1855                1860
```

-continued

```
Asp Gln Ala Ser Gly Asn Val Lys Lys Ala Leu Lys Leu Met Gly
    1865                1870                1875
Ser Asn Glu Gly Glu Phe Lys Ala Glu Gly Asn Ser Lys Phe Thr
    1880                1885                1890
Tyr Thr Val Leu Glu Asp Gly Cys Thr Lys His Thr Gly Glu Trp
    1895                1900                1905
Ser Lys Thr Val Phe Glu Tyr Arg Thr Arg Lys Ala Val Arg Leu
    1910                1915                1920
Pro Ile Val Asp Ile Ala Pro Tyr Asp Ile Gly Gly Pro Asp Gln
    1925                1930                1935
Glu Phe Gly Val Asp Val Gly Pro Val Cys Phe Leu
    1940                1945                1950

<210> SEQ ID NO 11
<211> LENGTH: 37
<212> TYPE: DNA
<213> ORGANISM: Artificial Sequence
<220> FEATURE:
<223> OTHER INFORMATION: Oligonucleotide for PCR

<400> SEQUENCE: 11
gcttccagtc ttccgagcat gccaaaataa tagtggg                          37

<210> SEQ ID NO 12
<211> LENGTH: 37
<212> TYPE: DNA
<213> ORGANISM: Artificial Sequence
<220> FEATURE:
<223> OTHER INFORMATION: Oligonucleotide for PCR

<400> SEQUENCE: 12
cccactatta ttttggcatg ctcggaagac tggaagc                          37

<210> SEQ ID NO 13
<211> LENGTH: 4815
<212> TYPE: DNA
<213> ORGANISM: Artificial Sequence
<220> FEATURE:
<223> OTHER INFORMATION: DNA molecule based on procollagen type III
      N-propeptide. Sequence prior to N100 replaced with the sequence
      for the G3 domain of the alpha3 chain of laminin-5 whilst
      retaining the collagen III signal sequence.

<400> SEQUENCE: 13
atgatgagct ttgtgcaaaa ggggagctgg ctacttctcg ctctgcttca tcccactatt    60
attttggcat gctcggaaga ctggaagctt gtgcgatctg cctcattctc cagaggagga   120
caattgagtt tcactgattt gggcttacca cctactgacc acctccaggc tcatttggaa   180
tttcagacct ttcaacccag tggcatatta ttagatcatc agacatggac aaggaacctg   240
caggtcactc tggaagatgg ttacattgaa ttgagcacca gcgatagcgg cggcccaatt   300
tttaaatctc cacagacgta tatggatggt ttactgcatt atgtatctgt aataagcgac   360
aactctggac tacggcttct catcgatgac cagcttctga aaatagcaa aaggctaaaa   420 cacatttcaa gttcccggca gtctctgcgt ctgggcggga gcaattttga gggttgtatt   480
agcaatgttt ttgtccagag ttatcactg agtcctgaag tcctagattt gaccagtaac   540
tctctcaaga gagatgtgtc cctgggaggc tgcagtttaa acaaaccacc ttttctaatg   600
ttgcttaaag ttctaccag gtttaacaag accaagactt tcgtatcaa ccagctgttg   660 caggacacac cagtggcctc cccaaggagc gtgaaggtgt ggcaagatgc taatggtcaa   720
```

```
ggacctcaag gccccaaggg agatccaggc cctcctggta ttcctgggag aaatggtgac    780
cctggtattc caggacaacc agggtcccct ggttctcctg gcccccctgg aatctgtgaa    840
tcatgcccta ctggtcctca gaactattct ccccagtatg attcatatga tgtcaagtct    900
ggagtagcag taggaggact cgcaggctat cctggaccag ctggcccccc aggccctccc    960
ggtcccctg gtacatctgg tcatcctggt tccctggat ctccaggata ccaaggaccc     1020
cctggtgaac ctgggcaagc tggtccttca ggccctccag acctcctggg tgctataggt   1080
ccatctggtc ctgctggaaa agatggagaa tcaggtagac ccggacgacc tggagagcga   1140
ggattgcctg gacctccagg tatcaaaggt ccagctggga tacctggatt ccctggtatg   1200
aaaggacaca gaggcttcga tggacgaaat ggagaaaagg gtgaaacagg tgctcctgga   1260
ttaaagggtg aaaatggtct tccaggcgaa aatggagctc ctggacccat gggtccaaga   1320
ggggctcctg gtgagcgagg acggccagga cttcctgggg ctgcaggtgc tcggggtaat   1380
gacggtgctc gaggcagtga tggtcaacca ggccctcctg gtcctcctgg aactgccgga   1440
ttccctggat cccctggtgc taagggtgaa gttggacctg cagggtctcc tggttcaaat   1500
ggtgcccctg gacaaagagg agaacctgga cctcagggac acgctggtgc tcaaggtcct   1560
cctggccctc ctgggattaa tggtagtcct ggtggtaaag gcgaaatggg tcccgctggc   1620
attcctggag ctcctggact gatgggagcc cggggtcctc caggaccagc cggtgctaat   1680
ggtgctcctg gactgcgagg tggtgcaggt gagcctggta agaatggtgc caaaggagag   1740
cccggaccac gtggtgaacg cggtgaggct ggtattccag tgttccagg agctaaaggc    1800
gaagatggca aggatggatc acctggagaa cctggtgcaa atgggcttcc aggagctgca   1860
ggagaaaggg gtgcccctgg gttccgagga cctgctggac aaatggcat cccaggagaa    1920
aagggtcctg ctggagagcg tggtgctcca ggccctgcag ggcccagagg agctgctgga   1980
gaacctggca gagatggcgt ccctggaggt ccaggaatga gggcatgcc cggaagtcca    2040
ggaggaccag gaagtgatgg gaaaccaggg cctcccggaa gtcaaggaga agtggtcga    2100
ccaggtcctc ctgggccatc tggtcccga ggtcagcctg gtgtcatggg cttcccggt     2160
cctaaaggaa atgatggtgc tcctggtaag aatggagaac aggtggccc tggaggacct    2220
ggccctcagg gtcctcctgg aaagaatggt gaaactggac ctcaaggacc cccagggcct   2280
actgggcctg gtggtgacaa aggagacaca ggaccccctg gtccacaagg attacaaggc   2340
ttgcctggta caggtggtcc tcaggagaaa atggaaaac ctgggaacc aggtccaaag     2400
ggtgatgccg gtgcacctgg agctccagga ggcaagggtg atgctggtgc ccctggtgaa   2460
cgtggacctc ctggattggc aggggcccca ggacttagag gtgagctgg tcccctggt     2520
cccgaaggag gaaagggtgc tgctggtcct cctgggccac ctggtgctgc tggtactcct   2580
ggtctgcaag gaatgcctgg agaaagagga ggtcttggaa gtcctggtcc aaagggtgac   2640
aagggtgaac caggcggccc aggtgctgat ggtgtcccag ggaaagatgg ccaaggggt    2700
cctactggtc ctattggtcc tctggcccaa gctggccagc ctggagataa gggtgaaggt   2760
ggtgcccccg gacttccagg tatagctgga cctcgtggta gccctggtga gagaggtgaa   2820
actggccctc caggacctgc tggttttccct ggtgctcctg gacagaatgg tgaacctggt   2880
ggtaaaggag aaagaggggc tccgggtgag aaaggtgaag aggccctcc tggagttgca    2940
ggaccccctg gaggttctgg acctgctggt cctcctggtc cccaaggtgt caaaggtgaa   3000
cgtggcagtc ctggtggacc tggtgctgct ggcttcctg gtgctcgtgg tcttcctggt   3060
```

-continued

```
cctcctggta gtaatggtaa cccaggaccc ccaggtccca gcggttctcc aggcaaggat    3120
gggcccccag gtcctgcggg taacactggt gctcctggca gccctggagt gtctggacca    3180
aaaggtgatg ctggccaacc aggagagaag ggatcgcctg gtgcccaggg cccaccagga    3240
gctccaggcc cacttgggat tgctgggatc actggagcac ggggtcttgc aggaccacca    3300
ggcatgccag gtcctagggg aagccctggc cctcagggtg tcaagggtga agtgggaaa     3360 ccaggagcta acggtctcag tggagaacgt ggtccccctg accccaggg tcttcctggt     3420 ctggctggta cagctggtga acctggaaga gatggaaacc ctggatcaga tggtcttcca    3480
ggccgagatg gatctcctgg tggcaagggt gatcgtggtg aaaatggctc tcctggtgcc    3540
cctggcgctc ctggtcatcc aggcccacct ggtcctgtcg gtccagctgg aaagagtggt    3600
gacagaggag aaagtggccc tgctggccct gctggtgctc ccggtcctgc tggttcccga    3660
ggtgctcctg gtcctcaagg cccacgtggt gacaaggtg aaacaggtga acgtggagct    3720
gctggcatca aggacatcg aggattccct ggtaatccag gtgccccagg ttctccaggc    3780
cctgctggtc agcagggtgc aatcggcagt ccaggacctg caggccccag aggacctgtt    3840
ggacccagtg gacctcctgg caaagatgga accagtggac atccaggtcc cattggacca    3900
ccagggcctc gaggtaacag aggtgaaaga ggatctgagg gctccccagg ccacccaggg    3960
caaccaggcc ctcctggacc tcctggtgcc cctggtcctt gctgtggtgg tgttggagcc    4020
gctgccattg ctgggattgg aggtgaaaa gctggcggtt ttgccccgta ttatggagat    4080
gaaccaatgg atttcaaaat caacaccgat gagattatga cttcactcaa gtctgttaat    4140
ggacaaatag aaagcctcat tagtcctgat ggttctcgta aaacccccgc tagaaactgc    4200
agagacctga aattctgcca tcctgaactc aagagtggag aatactgggt tgaccctaac    4260
caaggatgca aattggatgc tatcaaggta ttctgtaata tggaaactgg ggaaacatgc    4320
ataagtgcca atccttttga tgttccacgg aaacactggt ggacagattc tagtgctgag    4380
aagaaacacg tttggttggg agagtccatg gatggtggtt tcagtttag ctacggcaat    4440 cctgaacttc ctgaagatgt ccttgatgtg cagctggcat tccttcgact tctctccagc    4500
cgagcttccc agaacatcac atatcactgc aaaaatagca ttgcatacat ggatcaggcc    4560
agtggaaatg taaagaaggc cctgaagctg atggggtcaa atgaaggtga attcaaggct    4620
gaaggaaata gcaaattcac ctacacagtt ctggaggatg gttgcacgaa acacactggg    4680
gaatggagca aaacagtctt tgaatatcga acacgcaagg ctgtgagact acctattgta    4740
gatattgcac cctatgacat tggtggtcct gatcaagaat ttggtgtgga cgttggccct    4800
gtttgctttt tataa                                                    4815
```

<210> SEQ ID NO 14
<211> LENGTH: 1604
<212> TYPE: PRT
<213> ORGANISM: Artificial Sequence
<220> FEATURE:
<223> OTHER INFORMATION: Sequence of modified pro-alpha chain.

<400> SEQUENCE: 14

```
Met Met Ser Phe Val Gln Lys Gly Ser Trp Leu Leu Leu Ala Leu Leu
1               5                   10                  15

His Pro Thr Ile Ile Leu Ala Cys Ser Glu Asp Trp Lys Leu Val Arg
            20                  25                  30

Ser Ala Ser Phe Ser Arg Gly Gly Gln Leu Ser Phe Thr Asp Leu Gly
        35                  40                  45
```

-continued

```
Leu Pro Pro Thr Asp His Leu Gln Ala Ser Phe Gly Phe Gln Thr Phe
     50                  55                  60

Gln Pro Ser Gly Ile Leu Leu Asp His Gln Thr Trp Thr Arg Asn Leu
 65                  70                  75                  80

Gln Val Thr Leu Glu Asp Gly Tyr Ile Glu Leu Ser Thr Ser Asp Ser
                 85                  90                  95

Gly Gly Pro Ile Phe Lys Ser Pro Gln Thr Tyr Met Asp Gly Leu Leu
            100                 105                 110

His Tyr Val Ser Val Ile Ser Asp Asn Ser Gly Leu Arg Leu Leu Ile
            115                 120                 125

Asp Asp Gln Leu Leu Arg Asn Ser Lys Arg Leu Lys His Ile Ser Ser
    130                 135                 140

Ser Arg Gln Ser Leu Arg Leu Gly Gly Ser Asn Phe Glu Gly Cys Ile
145                 150                 155                 160

Ser Asn Val Phe Val Gln Arg Leu Ser Leu Ser Pro Glu Val Leu Asp
                165                 170                 175

Leu Thr Ser Asn Ser Leu Lys Arg Asp Val Ser Leu Gly Gly Cys Ser
            180                 185                 190

Leu Asn Lys Pro Pro Phe Leu Met Leu Leu Lys Gly Ser Thr Arg Phe
            195                 200                 205

Asn Lys Thr Lys Thr Phe Arg Ile Asn Gln Leu Leu Gln Asp Thr Pro
    210                 215                 220

Val Ala Ser Pro Arg Ser Val Lys Val Trp Gln Asp Ala Asn Gly Gln
225                 230                 235                 240

Gly Pro Gln Gly Pro Lys Gly Asp Pro Gly Pro Gly Ile Pro Gly
                245                 250                 255

Arg Asn Gly Asp Pro Gly Ile Pro Gly Gln Pro Gly Ser Pro Gly Ser
            260                 265                 270

Pro Gly Pro Pro Gly Ile Cys Glu Ser Cys Pro Thr Gly Pro Gln Asn
            275                 280                 285

Tyr Ser Pro Gln Tyr Asp Ser Tyr Asp Val Lys Ser Gly Val Ala Val
    290                 295                 300

Gly Gly Leu Ala Gly Tyr Pro Gly Pro Ala Gly Pro Pro Gly Pro Pro
305                 310                 315                 320

Gly Pro Pro Gly Thr Ser Gly His Pro Gly Ser Pro Gly Ser Pro Gly
                325                 330                 335

Tyr Gln Gly Pro Pro Gly Glu Pro Gly Gln Ala Gly Pro Ser Gly Pro
            340                 345                 350

Pro Gly Pro Pro Gly Ala Ile Gly Pro Ser Gly Pro Ala Gly Lys Asp
            355                 360                 365

Gly Glu Ser Gly Arg Pro Gly Arg Pro Gly Glu Arg Gly Leu Pro Gly
    370                 375                 380

Pro Pro Gly Ile Lys Gly Pro Ala Gly Ile Pro Gly Phe Pro Gly Met
385                 390                 395                 400

Lys Gly His Arg Gly Phe Asp Gly Arg Asn Gly Glu Lys Gly Glu Thr
                405                 410                 415

Gly Ala Pro Gly Leu Lys Gly Glu Asn Gly Leu Pro Gly Glu Asn Gly
            420                 425                 430

Ala Pro Gly Pro Met Gly Pro Arg Gly Ala Pro Gly Glu Arg Gly Arg
            435                 440                 445

Pro Gly Leu Pro Gly Ala Ala Gly Ala Arg Gly Asn Asp Gly Ala Arg
    450                 455                 460

Gly Ser Asp Gly Gln Pro Gly Pro Pro Gly Pro Pro Gly Thr Ala Gly
```

-continued

```
              465                 470                 475                 480

Phe Pro Gly Ser Pro Gly Ala Lys Gly Glu Val Gly Pro Ala Gly Ser
                          485                 490                 495

Pro Gly Ser Asn Gly Ala Pro Gly Gln Arg Gly Glu Pro Gly Pro Gln
                          500                 505                 510

Gly His Ala Gly Ala Gln Gly Pro Gly Pro Pro Gly Ile Asn Gly
                          515                 520                 525

Ser Pro Gly Gly Lys Gly Glu Met Gly Pro Ala Gly Ile Pro Gly Ala
                          530                 535                 540

Pro Gly Leu Met Gly Ala Arg Gly Pro Gly Pro Ala Gly Ala Asn
          545                 550                 555                 560

Gly Ala Pro Gly Leu Arg Gly Ala Gly Glu Pro Gly Lys Asn Gly
                          565                 570                 575

Ala Lys Gly Glu Pro Gly Pro Arg Gly Glu Arg Gly Glu Ala Gly Ile
                          580                 585                 590

Pro Gly Val Pro Gly Ala Lys Gly Glu Asp Gly Lys Asp Gly Ser Pro
                          595                 600                 605

Gly Glu Pro Gly Ala Asn Gly Leu Pro Gly Ala Ala Gly Glu Arg Gly
                          610                 615                 620

Ala Pro Gly Phe Arg Gly Pro Ala Gly Pro Asn Gly Ile Pro Gly Glu
          625                 630                 635                 640

Lys Gly Pro Ala Gly Glu Arg Gly Ala Pro Gly Pro Ala Gly Pro Arg
                          645                 650                 655

Gly Ala Ala Gly Glu Pro Gly Arg Asp Gly Val Pro Gly Pro Gly
                          660                 665                 670

Met Arg Gly Met Pro Gly Ser Pro Gly Gly Pro Gly Ser Asp Gly Lys
                          675                 680                 685

Pro Gly Pro Pro Gly Ser Gln Gly Glu Ser Gly Arg Pro Gly Pro Pro
                          690                 695                 700

Gly Pro Ser Gly Pro Arg Gly Gln Pro Gly Val Met Gly Phe Pro Gly
          705                 710                 715                 720

Pro Lys Gly Asn Asp Gly Ala Pro Gly Lys Asn Gly Glu Arg Gly Gly
                          725                 730                 735

Pro Gly Gly Pro Gly Pro Gln Gly Pro Pro Gly Lys Asn Gly Glu Thr
                          740                 745                 750

Gly Pro Gln Gly Pro Pro Gly Pro Thr Gly Pro Gly Gly Asp Lys Gly
                          755                 760                 765

Asp Thr Gly Pro Pro Gly Pro Gln Gly Leu Gln Gly Leu Pro Gly Thr
                          770                 775                 780

Gly Gly Pro Pro Gly Glu Asn Gly Lys Pro Gly Glu Pro Gly Pro Lys
          785                 790                 795                 800

Gly Asp Ala Gly Ala Pro Gly Ala Pro Gly Gly Lys Gly Asp Ala Gly
                          805                 810                 815

Ala Pro Gly Glu Arg Gly Pro Pro Gly Leu Ala Gly Ala Pro Gly Leu
                          820                 825                 830

Arg Gly Gly Ala Gly Pro Pro Gly Pro Glu Gly Gly Lys Gly Ala Ala
                          835                 840                 845

Gly Pro Pro Gly Pro Pro Gly Ala Ala Gly Thr Pro Gly Leu Gln Gly
                          850                 855                 860

Met Pro Gly Glu Arg Gly Gly Leu Gly Ser Pro Gly Pro Lys Gly Asp
          865                 870                 875                 880

Lys Gly Glu Pro Gly Gly Pro Gly Ala Asp Gly Val Pro Gly Lys Asp
                          885                 890                 895
```

```
Gly Pro Arg Gly Pro Thr Gly Pro Ile Gly Pro Gly Pro Ala Gly
            900             905             910

Gln Pro Gly Asp Lys Gly Glu Gly Ala Pro Gly Leu Pro Gly Ile
            915             920             925

Ala Gly Pro Arg Gly Ser Pro Gly Glu Arg Gly Glu Thr Gly Pro Pro
930             935             940

Gly Pro Ala Gly Phe Pro Gly Ala Pro Gly Gln Asn Gly Glu Pro Gly
945             950             955             960

Gly Lys Gly Glu Arg Gly Ala Pro Gly Glu Lys Gly Glu Gly Gly Pro
            965             970             975

Pro Gly Val Ala Gly Pro Pro Gly Ser Gly Pro Ala Gly Pro Pro
            980             985             990

Gly Pro Gln Gly Val Lys Gly Glu Arg Gly Ser Pro Gly Gly Pro Gly
            995             1000            1005

Ala Ala Gly Phe Pro Gly Ala Arg Gly Leu Pro Gly Pro Pro Gly
    1010            1015            1020

Ser Asn Gly Asn Pro Gly Pro Pro Gly Pro Ser Gly Ser Pro Gly
    1025            1030            1035

Lys Asp Gly Pro Pro Gly Pro Ala Gly Asn Thr Gly Ala Pro Gly
    1040            1045            1050

Ser Pro Gly Val Ser Gly Pro Lys Gly Asp Ala Gly Gln Pro Gly
    1055            1060            1065

Glu Lys Gly Ser Pro Gly Ala Gln Gly Pro Pro Gly Ala Pro Gly
    1070            1075            1080

Pro Leu Gly Ile Ala Gly Ile Thr Gly Ala Arg Gly Leu Ala Gly
    1085            1090            1095

Pro Pro Gly Met Pro Gly Pro Arg Gly Ser Pro Gly Pro Gln Gly
    1100            1105            1110

Val Lys Gly Glu Ser Gly Lys Pro Gly Ala Asn Gly Leu Ser Gly
    1115            1120            1125

Glu Arg Gly Pro Pro Gly Pro Gln Gly Leu Pro Gly Leu Ala Gly
    1130            1135            1140

Thr Ala Gly Glu Pro Gly Arg Asp Gly Asn Pro Gly Ser Asp Gly
    1145            1150            1155

Leu Pro Gly Arg Asp Gly Ser Pro Gly Gly Lys Gly Asp Arg Gly
    1160            1165            1170

Glu Asn Gly Ser Pro Gly Ala Pro Gly Ala Pro Gly His Pro Gly
    1175            1180            1185

Pro Pro Gly Pro Val Gly Pro Ala Gly Lys Ser Gly Asp Arg Gly
    1190            1195            1200

Glu Ser Gly Pro Ala Gly Pro Ala Gly Ala Pro Gly Pro Ala Gly
    1205            1210            1215

Ser Arg Gly Ala Pro Gly Pro Gln Gly Pro Arg Gly Asp Lys Gly
    1220            1225            1230

Glu Thr Gly Glu Arg Gly Ala Ala Gly Ile Lys Gly His Arg Gly
    1235            1240            1245

Phe Pro Gly Asn Pro Gly Ala Pro Gly Ser Pro Gly Pro Ala Gly
    1250            1255            1260

Gln Gln Gly Ala Ile Gly Ser Pro Gly Pro Ala Gly Pro Arg Gly
    1265            1270            1275

Pro Val Gly Pro Ser Gly Pro Pro Gly Lys Asp Gly Thr Ser Gly
    1280            1285            1290
```

-continued

```
His Pro Gly Pro Ile Gly Pro Pro Gly Pro Arg Gly Asn Arg Gly
    1295                1300                1305

Glu Arg Gly Ser Glu Gly Ser Pro Gly His Pro Gly Gln Pro Gly
    1310                1315                1320

Pro Pro Gly Pro Pro Gly Ala Pro Gly Pro Cys Cys Gly Gly Val
    1325                1330                1335

Gly Ala Ala Ala Ile Ala Gly Ile Gly Gly Glu Lys Ala Gly Gly
    1340                1345                1350

Phe Ala Pro Tyr Tyr Gly Asp Glu Pro Met Asp Phe Lys Ile Asn
    1355                1360                1365

Thr Asp Glu Ile Met Thr Ser Leu Lys Ser Val Asn Gly Gln Ile
    1370                1375                1380

Glu Ser Leu Ile Ser Pro Asp Gly Ser Arg Lys Asn Pro Ala Arg
    1385                1390                1395

Asn Cys Arg Asp Leu Lys Phe Cys His Pro Glu Leu Lys Ser Gly
    1400                1405                1410

Glu Tyr Trp Val Asp Pro Asn Gln Gly Cys Lys Leu Asp Ala Ile
    1415                1420                1425

Lys Val Phe Cys Asn Met Glu Thr Gly Glu Thr Cys Ile Ser Ala
    1430                1435                1440

Asn Pro Leu Asn Val Pro Arg Lys His Trp Trp Thr Asp Ser Ser
    1445                1450                1455

Ala Glu Lys Lys His Val Trp Phe Gly Glu Ser Met Asp Gly Gly
    1460                1465                1470

Phe Gln Phe Ser Tyr Gly Asn Pro Glu Leu Pro Glu Asp Val Leu
    1475                1480                1485

Asp Val Gln Leu Ala Phe Leu Arg Leu Leu Ser Ser Arg Ala Ser
    1490                1495                1500

Gln Asn Ile Thr Tyr His Cys Lys Asn Ser Ile Ala Tyr Met Asp
    1505                1510                1515

Gln Ala Ser Gly Asn Val Lys Lys Ala Leu Lys Leu Met Gly Ser
    1520                1525                1530

Asn Glu Gly Glu Phe Lys Ala Glu Gly Asn Ser Lys Phe Thr Tyr
    1535                1540                1545

Thr Val Leu Glu Asp Gly Cys Thr Lys His Thr Gly Glu Trp Ser
    1550                1555                1560

Lys Thr Val Phe Glu Tyr Arg Thr Arg Lys Ala Val Arg Leu Pro
    1565                1570                1575

Ile Val Asp Ile Ala Pro Tyr Asp Ile Gly Gly Pro Asp Gln Glu
    1580                1585                1590

Phe Gly Val Asp Val Gly Pro Val Cys Phe Leu
    1595                1600
```

<210> SEQ ID NO 15
<211> LENGTH: 37
<212> TYPE: DNA
<213> ORGANISM: Artificial Sequence
<220> FEATURE:
<223> OTHER INFORMATION: PCR primer

<400> SEQUENCE: 15
cttgtagatg cggccgcatg aagtccagcg gcctctt       37

<210> SEQ ID NO 16
<211> LENGTH: 30
<212> TYPE: DNA

```
<213> ORGANISM: Artificial Sequence
<220> FEATURE:
<223> OTHER INFORMATION: PCR primer

<400> SEQUENCE: 16
cttcaacagc agctttcaca ggggaaacgc                                      30

<210> SEQ ID NO 17
<211> LENGTH: 30
<212> TYPE: DNA
<213> ORGANISM: Artificial Sequence
<220> FEATURE:
<223> OTHER INFORMATION: PCR primer

<400> SEQUENCE: 17
tgtgaaagct gctgttgaag gaggatgttc                                      30

<210> SEQ ID NO 18
<211> LENGTH: 20
<212> TYPE: DNA
<213> ORGANISM: Artificial Sequence
<220> FEATURE:
<223> OTHER INFORMATION: PCR primer

<400> SEQUENCE: 18
ggacctggtc gaccactttc                                                 20

<210> SEQ ID NO 19
<211> LENGTH: 22
<212> TYPE: DNA
<213> ORGANISM: Artificial Sequence
<220> FEATURE:
<223> OTHER INFORMATION: PCR primer

<400> SEQUENCE: 19
gtaatacgac tcactatagg gc                                              22

<210> SEQ ID NO 20
<211> LENGTH: 18
<212> TYPE: DNA
<213> ORGANISM: Artificial Sequence
<220> FEATURE:
<223> OTHER INFORMATION: PCR primer

<400> SEQUENCE: 20
gctgttgaag gaggatgt                                                   18

<210> SEQ ID NO 21
<211> LENGTH: 18
<212> TYPE: DNA
<213> ORGANISM: Artificial Sequence
<220> FEATURE:
<223> OTHER INFORMATION: PCR primer

<400> SEQUENCE: 21
agaggcttcg atggacga                                                   18

<210> SEQ ID NO 22
<211> LENGTH: 18
<212> TYPE: DNA
<213> ORGANISM: Artificial Sequence
<220> FEATURE:
<223> OTHER INFORMATION: PCR primer

<400> SEQUENCE: 22
ggactgcgag gtggtgca                                                   18
```

<210> SEQ ID NO 23
<211> LENGTH: 18
<212> TYPE: DNA
<213> ORGANISM: Artificial Sequence
<220> FEATURE:
<223> OTHER INFORMATION: PCR primer

<400> SEQUENCE: 23
ttctcccagg aataccag                                                       18

<210> SEQ ID NO 24
<211> LENGTH: 18
<212> TYPE: DNA
<213> ORGANISM: Artificial Sequence
<220> FEATURE:
<223> OTHER INFORMATION: PCR primer

<400> SEQUENCE: 24
agggaatccg gcagttcc                                                       18

<210> SEQ ID NO 25
<211> LENGTH: 18
<212> TYPE: DNA
<213> ORGANISM: Artificial Sequence
<220> FEATURE:
<223> OTHER INFORMATION: PCR primer

<400> SEQUENCE: 25
ctcggggacc agatggcc                                                       18

<210> SEQ ID NO 26
<211> LENGTH: 4719
<212> TYPE: DNA
<213> ORGANISM: Artificial Sequence
<220> FEATURE:
<223> OTHER INFORMATION: DNA molecule based on procollagen type III
      N-propeptide. Procollagen type III N-propeptide sequence replaced
      with the sequence for SLPI whilst retaining the collagen III
      signal sequence.

<400> SEQUENCE: 26

| | | |
|---|---|---|
| atgaagtcca gcggcctctt cccctccctg gtgctgcttg ccctgggaac tctggcacct | 60 |
| tgggctgtgg aaggctctgg aaagtccttc aaagctggag tctgtcctcc taagaaatct | 120 |
| gcccagtgcc ttagatacaa gaaacctgag tgccagagtg actggcagtg tccagggaag | 180 |
| aagagatgtt gtcctgacac ttgtggcatc aaatgcctgg atcctgttga caccccaaac | 240 |
| ccaacaagga ggaagcctgg gaagtgccca gtgacttatg ccaatgtttt gatgcttaac | 300 |
| ccccccaatt tctgtgagat ggatggccag tgcaagcgtg acttgaagtg ttgcatgggc | 360 |
| atgtgtggga atcctgcgt ttcccctgtg aaagctgctg ttgaaggagg atgttcccat | 420 |
| cttggtcagt cctatgcgga tagagatgtc tggaagccag aaccatgcca aatatgtgtc | 480 |
| tgtgactcag gatccgttct ctgcgatgac ataatatgtg acgatcaaga attagactgc | 540 |
| cccaacccag aaattccatt tggagaatgt tgtgcagttt gcccacagcc tccaactgct | 600 |
| cctactcgcc ctcctaatgg tcaaggacct caaggcccca agggagatcc aggccctcct | 660 |
| ggtattcctg ggagaaatgg tgaccctggt attccaggac aaccagggtc ccctggttct | 720 |
| cctggccccc ctggaatctg tgaatcatgc cctactggtc tcagaacta ttctccccag | 780 |
| tatgattcat atgatgtcaa gtctggagta gcagtaggag gactcgcagg ctatcctgga | 840 |
| ccagctggcc cccaggccc tccggtccc ctggtacat ctggtcatcc tggttcccct | 900 |

```
ggatctccag gataccaagg accccctggt gaacctgggc aagctggtcc ttcaggccct    960
ccaggacctc ctggtgctat aggtccatct ggtcctgctg gaaaagatgg agaatcaggt   1020
agacccggac gacctggaga gcgaggattg cctggacctc caggtatcaa aggtccagct   1080
gggatacctg gattccctgg tatgaaagga cacagaggct tcgatggacg aaatggagaa   1140
aagggtgaaa caggtgctcc tggattaaag ggtgaaaatg gtcttccagg cgaaaatgga   1200
gctcctggac ccatgggtcc aagaggggct cctggtgagc gaggacggcc aggacttcct   1260
ggggctgcag gtgctcgggg taatgacggt gctcgaggca gtgatggtca accaggccct   1320
cctggtcctc ctggaactgc cggattccct ggatccctg gtgctaaggg tgaagttgga   1380
cctgcagggt ctcctggttc aaatggtgcc cctggacaaa gaggagaacc tggacctcag   1440
ggacacgctg gtgctcaagg tcctcctggc cctcctggga ttaatggtag tcctggtggt   1500
aaaggcgaaa tggtcccgc tggcattcct ggagctcctg gactgatggg agcccggggt   1560
cctccaggac cagccggtgc taatggtgct cctggactgc gaggtggtgc aggtgagcct   1620
ggtaagaatg gtgccaaagg agagcccgga ccacgtggtg aacgcggtga ggctggtatt   1680
ccaggtgttc caggagctaa aggcgaagat ggcaaggatg gatcacctgg agaacctggt   1740
gcaaatgggc ttccaggagc tgcaggagaa aggggtgccc ctgggttccg aggacctgct   1800
ggaccaaatg gcatcccagg agaaaagggt cctgctggag agcgtggtgc tccaggccct   1860
gcagggccca ggagctgc tggagaacct ggcagagatg gcgtccctgg aggtccagga   1920
atgaggggca tgcccggaag tccaggagga ccaggaagta tgggaaacc agggcctccc   1980
ggaagtcaag gagaaagtgg tcgaccaggt cctcctgggc catctggtcc ccgaggtcag   2040
cctggtgtca tgggcttccc cggtcctaaa ggaaatgatg gtgctcctgg taagaatgga   2100
gaacgaggtg gccctggagg acctggccct cagggtcctc ctggaaagaa tggtgaaact   2160
ggacctcaag gaccccagg gcctactggg cctggtggta caaaggaga cacaggaccc   2220
cctggtccac aaggattaca aggcttgcct ggtacaggtg gtcctccagg agaaaatgga   2280
aaacctgggg aaccaggtcc aaagggtgat gccggtgcac ctggagctcc aggaggcaag   2340
ggtgatgctg gtgcccctgg tgaacgtgga cctcctggat tggcaggggc cccaggactt   2400
agaggtggag ctggtcccc tggtcccgaa ggaggaaagg gtgctgctgg tcctcctggg   2460
ccacctggtg ctgctggtac tcctggtctg caaggaatgc ctggagaaag aggaggtctt   2520
ggaagtcctg gtcaaagggt tgacaagggt gaaccaggcg gcccaggtgc tgatggtgtc   2580
ccagggaaag atgggcccaag gggtcctact ggtcctattg gtcctcctgg cccagctggc   2640
cagcctggga taagggtga agtggtgcc cccggacttc caggtatagc tggacctcgt   2700
ggtagccctg gtgagagagg tgaaactggc cctccaggac ctgctggttt ccctggtgct   2760
cctggacaga atggtgaacc tggtggtaaa ggagaaagag gggctccggg tgagaaaggt   2820
gaaggaggcc ctcctggagt tgcaggaccc cctggaggtt ctggacctgc tggtcctcct   2880
ggtcccaag gtgtcaaagg tgaacgtggc agtcctggtg gacctggtgc tgctggcttc   2940
cctggtgctc gtggtcttcc tggtcctcct ggtagtaatg gtaacccagg acccccaggt   3000
cccagcggtt ctccaggcaa ggatgggccc caggtcctg cggtaacac tggtgctcct   3060
ggcagccctg gagtgtctgg accaaaaggt gatgctggcc aaccaggaga aagggatcg   3120
cctggtgccc agggcccacc aggagctcca ggcccacttg ggattgctgg gatcactgga   3180
gcacggggtc ttgcaggacc accaggcatg ccaggtccta ggggaagccc tggccctcag   3240
```

```
ggtgtcaagg gtgaaagtgg gaaaccagga gctaacggtc tcagtggaga acgtggtccc      3300
cctggacccc agggtcttcc tggtctggct ggtacagctg tgaacctgg aagagatgga      3360 aaccctggat cagatggtct tccaggccga gatggatctc ctggtggcaa gggtgatcgt      3420
ggtgaaaatg gctctcctgg tgcccctggc gctcctggta tccaggccc acctggtcct      3480 gtcggtccag ctggaaagag tggtgacaga ggagaaagtg gccctgctgg ccctgctggt      3540
gctcccggtc ctgctggttc ccgaggtgct cctggtcctc aaggcccacg tggtgacaaa      3600
ggtgaaacag gtgaacgtgg agctgctggc atcaaaggac atcgaggatt ccctggtaat      3660
ccaggtgccc caggttctcc aggccctgct ggtcagcagg gtgcaatcgg cagtccagga      3720
cctgcaggcc ccagaggacc tgttggaccc agtggacctc ctggcaaaga tggaaccagt      3780
ggacatccag gtcccattgg accaccaggg cctcgaggta acagaggtga agaggatct      3840 gagggctccc caggccaccc agggcaacca ggccctcctg gacctcctgg tgcccctggt      3900
ccttgctgtg gtggtgttgg agccgctgcc attgctggga ttggaggtga aaaagctggc      3960
ggttttgccc cgtattatgg agatgaacca atggatttca aaatcaacac cgatgagatt      4020
atgacttcac tcaagtctgt taatggacaa atagaaagcc tcattagtcc tgatggttct      4080
cgtaaaaacc ccgctagaaa ctgcagagac ctgaaattct gccatcctga actcaagagt      4140
ggagaatact gggttgaccc taaccaagga tgcaaattgg atgctatcaa ggtattctgt      4200
aatatggaaa ctggggaaac atgcataagt gccaatcctt gaatgttcc acggaaacac      4260 tggtggacag attctagtgc tgagaagaaa cacgtttggt ttggagagtc catggatggt      4320
ggttttcagt ttagctacgg caatcctgaa cttcctgaag atgtccttga tgtgcagctg      4380
gcattccttc gacttctctc cagccgagct cccagaaca tcacatatca ctgcaaaaat      4440
agcattgcat acatggatca ggccagtgga aatgtaaaga aggccctgaa gctgatgggg      4500
tcaaatgaag gtgaattcaa ggctgaagga aatagcaaat tcacctacac agttctggag      4560
gatggttgca cgaaacacac tggggaatgg agcaaaacag tctttgaata tcgaacacgc      4620
aaggctgtga gactacctat tgtagatatt gcaccctatg acattggtgg tcctgatcaa      4680
gaatttggtg tggacgttgg ccctgtttgc ttttataa                              4719
```

<210> SEQ ID NO 27
<211> LENGTH: 1572
<212> TYPE: PRT
<213> ORGANISM: Artificial Sequence
<220> FEATURE:
<223> OTHER INFORMATION: Sequence of modified pro-alpha chain.

<400> SEQUENCE: 27

Met Lys Ser Ser Gly Leu Phe Pro Phe Leu Val Leu Leu Ala Leu Gly
1               5                   10                  15

Thr Leu Ala Pro Trp Ala Val Glu Gly Ser Gly Lys Ser Phe Lys Ala
            20                  25                  30

Gly Val Cys Pro Pro Lys Lys Ser Ala Gln Cys Leu Arg Tyr Lys Lys
        35                  40                  45

Pro Glu Cys Gln Ser Asp Trp Gln Cys Pro Gly Lys Lys Arg Cys Cys
    50                  55                  60

Pro Asp Thr Cys Gly Ile Lys Cys Leu Asp Pro Val Asp Thr Pro Asn
65                  70                  75                  80

Pro Thr Arg Arg Lys Pro Gly Lys Cys Pro Val Thr Tyr Gly Gln Cys
                85                  90                  95

-continued

```
Leu Met Leu Asn Pro Pro Asn Phe Cys Glu Met Asp Gly Gln Cys Lys
            100                 105                 110

Arg Asp Leu Lys Cys Cys Met Gly Met Cys Gly Lys Ser Cys Val Ser
            115                 120                 125

Pro Val Lys Ala Ala Val Glu Gly Gly Cys Ser His Leu Gly Gln Ser
            130                 135                 140

Tyr Ala Asp Arg Asp Val Trp Lys Pro Glu Pro Cys Gln Ile Cys Val
145                 150                 155                 160

Cys Asp Ser Gly Ser Val Leu Cys Asp Asp Ile Ile Cys Asp Asp Gln
                165                 170                 175

Glu Leu Asp Cys Pro Asn Pro Glu Ile Pro Phe Gly Glu Cys Cys Ala
            180                 185                 190

Val Cys Pro Gln Pro Pro Thr Ala Pro Thr Arg Pro Pro Asn Gly Gln
            195                 200                 205

Gly Pro Gln Gly Pro Lys Gly Asp Pro Gly Pro Pro Gly Ile Pro Gly
            210                 215                 220

Arg Asn Gly Asp Pro Gly Ile Pro Gly Gln Pro Gly Ser Pro Gly Ser
225                 230                 235                 240

Pro Gly Pro Pro Gly Ile Cys Glu Ser Cys Pro Thr Gly Pro Gln Asn
                245                 250                 255

Tyr Ser Pro Gln Tyr Asp Ser Tyr Asp Val Lys Ser Gly Val Ala Val
            260                 265                 270

Gly Gly Leu Ala Gly Tyr Pro Gly Pro Ala Gly Pro Pro Gly Pro Pro
            275                 280                 285

Gly Pro Pro Gly Thr Ser Gly His Pro Gly Ser Pro Gly Ser Pro Gly
            290                 295                 300

Tyr Gln Gly Pro Pro Gly Glu Pro Gly Gln Ala Gly Pro Ser Gly Pro
305                 310                 315                 320

Pro Gly Pro Pro Gly Ala Ile Gly Pro Ser Gly Pro Ala Gly Lys Asp
                325                 330                 335

Gly Glu Ser Gly Arg Pro Gly Arg Pro Gly Glu Arg Gly Leu Pro Gly
            340                 345                 350

Pro Pro Gly Ile Lys Gly Pro Ala Gly Ile Pro Gly Phe Pro Gly Met
            355                 360                 365

Lys Gly His Arg Gly Phe Asp Gly Arg Asn Gly Glu Lys Gly Glu Thr
            370                 375                 380

Gly Ala Pro Gly Leu Lys Gly Glu Asn Gly Leu Pro Gly Glu Asn Gly
385                 390                 395                 400

Ala Pro Gly Pro Met Gly Pro Arg Gly Ala Pro Gly Glu Arg Gly Arg
                405                 410                 415

Pro Gly Leu Pro Gly Ala Ala Gly Ala Arg Gly Asn Asp Gly Ala Arg
            420                 425                 430

Gly Ser Asp Gly Gln Pro Gly Pro Pro Gly Pro Pro Gly Thr Ala Gly
            435                 440                 445

Phe Pro Gly Ser Pro Gly Ala Lys Gly Glu Val Gly Pro Ala Gly Ser
            450                 455                 460

Pro Gly Ser Asn Gly Ala Pro Gly Gln Arg Gly Glu Pro Gly Pro Gln
465                 470                 475                 480

Gly His Ala Gly Ala Gln Gly Pro Pro Gly Pro Pro Gly Ile Asn Gly
                485                 490                 495

Ser Pro Gly Gly Lys Gly Glu Met Gly Pro Ala Gly Ile Pro Gly Ala
            500                 505                 510
```

-continued

```
Pro Gly Leu Met Gly Ala Arg Gly Pro Pro Gly Ala Asn
        515                 520                 525
Gly Ala Pro Gly Leu Arg Gly Ala Gly Glu Pro Gly Lys Asn Gly
        530                 535                 540
Ala Lys Gly Glu Pro Gly Pro Arg Gly Glu Arg Gly Glu Ala Gly Ile
545                 550                 555                 560
Pro Gly Val Pro Gly Ala Lys Gly Glu Asp Gly Lys Asp Gly Ser Pro
                565                 570                 575
Gly Glu Pro Gly Ala Asn Gly Leu Pro Gly Ala Ala Gly Glu Arg Gly
                580                 585                 590
Ala Pro Gly Phe Arg Gly Pro Ala Gly Pro Asn Gly Ile Pro Gly Glu
        595                 600                 605
Lys Gly Pro Ala Gly Glu Arg Gly Ala Pro Gly Pro Ala Gly Pro Arg
        610                 615                 620
Gly Ala Ala Gly Glu Pro Gly Arg Asp Gly Val Pro Gly Gly Pro Gly
625                 630                 635                 640
Met Arg Gly Met Pro Gly Ser Pro Gly Gly Pro Gly Ser Asp Gly Lys
                645                 650                 655
Pro Gly Pro Pro Gly Ser Gln Gly Glu Ser Gly Arg Pro Gly Pro Pro
                660                 665                 670
Gly Pro Ser Gly Pro Arg Gly Gln Pro Gly Val Met Gly Phe Pro Gly
        675                 680                 685
Pro Lys Gly Asn Asp Gly Ala Pro Gly Lys Asn Gly Glu Arg Gly Gly
        690                 695                 700
Pro Gly Gly Pro Gly Pro Gln Gly Pro Pro Gly Lys Asn Gly Glu Thr
705                 710                 715                 720
Gly Pro Gln Gly Pro Pro Gly Pro Thr Gly Pro Gly Gly Asp Lys Gly
                725                 730                 735
Asp Thr Gly Pro Pro Gly Pro Gln Gly Leu Gln Gly Leu Pro Gly Thr
                740                 745                 750
Gly Gly Pro Pro Gly Glu Asn Gly Lys Pro Gly Glu Pro Gly Pro Lys
        755                 760                 765
Gly Asp Ala Gly Ala Pro Gly Ala Pro Gly Gly Lys Gly Asp Ala Gly
        770                 775                 780
Ala Pro Gly Glu Arg Gly Pro Pro Gly Leu Ala Gly Ala Pro Gly Leu
785                 790                 795                 800
Arg Gly Gly Ala Gly Pro Pro Gly Pro Glu Gly Gly Lys Gly Ala Ala
                805                 810                 815
Gly Pro Pro Gly Pro Pro Gly Ala Ala Gly Thr Pro Gly Leu Gln Gly
                820                 825                 830
Met Pro Gly Glu Arg Gly Gly Leu Gly Ser Pro Gly Pro Lys Gly Asp
        835                 840                 845
Lys Gly Glu Pro Gly Gly Pro Gly Ala Asp Gly Val Pro Gly Lys Asp
        850                 855                 860
Gly Pro Arg Gly Pro Thr Gly Pro Ile Gly Pro Pro Gly Pro Ala Gly
865                 870                 875                 880
Gln Pro Gly Asp Lys Gly Glu Gly Gly Ala Pro Gly Leu Pro Gly Ile
                885                 890                 895
Ala Gly Pro Arg Gly Ser Pro Gly Glu Arg Gly Glu Thr Gly Pro Pro
                900                 905                 910
Gly Pro Ala Gly Phe Pro Gly Ala Pro Gly Gln Asn Gly Glu Pro Gly
        915                 920                 925
```

-continued

```
Gly Lys Gly Glu Arg Gly Ala Pro Gly Glu Lys Glu Gly Gly Pro
        930                 935                 940

Pro Gly Val Ala Gly Pro Gly Gly Ser Gly Pro Ala Gly Pro Pro
945                 950                 955                 960

Gly Pro Gln Gly Val Lys Gly Glu Arg Gly Ser Pro Gly Pro Gly
                965                 970                 975

Ala Ala Gly Phe Pro Gly Ala Arg Gly Leu Pro Gly Pro Gly Ser
            980                 985                 990

Asn Gly Asn Pro Gly Pro Pro Gly Pro Ser Gly Ser Pro Gly Lys Asp
        995                 1000                 1005

Gly Pro Pro Gly Pro Ala Gly Asn Thr Gly Ala Pro Gly Ser Pro
    1010                1015                1020

Gly Val Ser Gly Pro Lys Gly Asp Ala Gly Gln Pro Gly Glu Lys
    1025                1030                1035

Gly Ser Pro Gly Ala Gln Gly Pro Pro Gly Ala Pro Gly Pro Leu
    1040                1045                1050

Gly Ile Ala Gly Ile Thr Gly Ala Arg Gly Leu Ala Gly Pro Pro
    1055                1060                1065

Gly Met Pro Gly Pro Arg Gly Ser Pro Gly Pro Gln Gly Val Lys
    1070                1075                1080

Gly Glu Ser Gly Lys Pro Gly Ala Asn Gly Leu Ser Gly Glu Arg
    1085                1090                1095

Gly Pro Pro Gly Pro Gln Gly Leu Pro Gly Leu Ala Gly Thr Ala
    1100                1105                1110

Gly Glu Pro Gly Arg Asp Gly Asn Pro Gly Ser Asp Gly Leu Pro
    1115                1120                1125

Gly Arg Asp Gly Ser Pro Gly Gly Lys Gly Asp Arg Gly Glu Asn
    1130                1135                1140

Gly Ser Pro Gly Ala Pro Gly Ala Pro Gly His Pro Gly Pro Pro
    1145                1150                1155

Gly Pro Val Gly Pro Ala Gly Lys Ser Gly Asp Arg Gly Glu Ser
    1160                1165                1170

Gly Pro Ala Gly Pro Ala Gly Ala Pro Gly Pro Ala Gly Ser Arg
    1175                1180                1185

Gly Ala Pro Gly Pro Gln Gly Pro Arg Gly Asp Lys Gly Glu Thr
    1190                1195                1200

Gly Glu Arg Gly Ala Ala Gly Ile Lys Gly His Arg Gly Phe Pro
    1205                1210                1215

Gly Asn Pro Gly Ala Pro Gly Ser Pro Gly Pro Ala Gly Gln Gln
    1220                1225                1230

Gly Ala Ile Gly Ser Pro Gly Pro Ala Gly Pro Arg Gly Pro Val
    1235                1240                1245

Gly Pro Ser Gly Pro Pro Gly Lys Asp Gly Thr Ser Gly His Pro
    1250                1255                1260

Gly Pro Ile Gly Pro Pro Gly Pro Arg Gly Asn Arg Gly Glu Arg
    1265                1270                1275

Gly Ser Glu Gly Ser Pro Gly His Pro Gly Gln Pro Gly Pro Pro
    1280                1285                1290

Gly Pro Pro Gly Ala Pro Gly Pro Cys Cys Gly Gly Val Gly Ala
    1295                1300                1305

Ala Ala Ile Ala Gly Ile Gly Gly Glu Lys Ala Gly Gly Phe Ala
    1310                1315                1320
```

```
Pro Tyr Tyr Gly Asp Glu Pro Met Asp Phe Lys Ile Asn Thr Asp
    1325                1330                1335

Glu Ile Met Thr Ser Leu Lys Ser Val Asn Gly Gln Ile Glu Ser
    1340                1345                1350

Leu Ile Ser Pro Asp Gly Ser Arg Lys Asn Pro Ala Arg Asn Cys
    1355                1360                1365

Arg Asp Leu Lys Phe Cys His Pro Glu Leu Lys Ser Gly Glu Tyr
    1370                1375                1380

Trp Val Asp Pro Asn Gln Gly Cys Lys Leu Asp Ala Ile Lys Val
    1385                1390                1395

Phe Cys Asn Met Glu Thr Gly Glu Thr Cys Ile Ser Ala Asn Pro
    1400                1405                1410

Leu Asn Val Pro Arg Lys His Trp Trp Thr Asp Ser Ser Ala Glu
    1415                1420                1425

Lys Lys His Val Trp Phe Gly Glu Ser Met Asp Gly Gly Phe Gln
    1430                1435                1440

Phe Ser Tyr Gly Asn Pro Glu Leu Pro Glu Asp Val Leu Asp Val
    1445                1450                1455

Gln Leu Ala Phe Leu Arg Leu Leu Ser Ser Arg Ala Ser Gln Asn
    1460                1465                1470

Ile Thr Tyr His Cys Lys Asn Ser Ile Ala Tyr Met Asp Gln Ala
    1475                1480                1485

Ser Gly Asn Val Lys Lys Ala Leu Lys Leu Met Gly Ser Asn Glu
    1490                1495                1500

Gly Glu Phe Lys Ala Glu Gly Asn Ser Lys Phe Thr Tyr Thr Val
    1505                1510                1515

Leu Glu Asp Gly Cys Thr Lys His Thr Gly Glu Trp Ser Lys Thr
    1520                1525                1530

Val Phe Glu Tyr Arg Thr Arg Lys Ala Val Arg Leu Pro Ile Val
    1535                1540                1545

Asp Ile Ala Pro Tyr Asp Ile Gly Gly Pro Asp Gln Glu Phe Gly
    1550                1555                1560

Val Asp Val Gly Pro Val Cys Phe Leu
    1565                1570

<210> SEQ ID NO 28
<211> LENGTH: 11
<212> TYPE: PRT
<213> ORGANISM: Unknown
<220> FEATURE:
<223> OTHER INFORMATION: Sequence typically found in small leucine-rich
      proteoglycans.
<220> FEATURE:
<221> NAME/KEY: MISC_FEATURE
<222> LOCATION: (2)..(3)
<223> OTHER INFORMATION: X at polition 2 or 3 may be any amino acid.
<220> FEATURE:
<221> NAME/KEY: MISC_FEATURE
<222> LOCATION: (5)..(5)
<223> OTHER INFORMATION: X at polition 5 may be any amino acid.
<220> FEATURE:
<221> NAME/KEY: MISC_FEATURE
<222> LOCATION: (7)..(8)
<223> OTHER INFORMATION: X at polition 7 or 8 may be any amino acid.
<220> FEATURE:
<221> NAME/KEY: MISC_FEATURE
<222> LOCATION: (10)..(10)
<223> OTHER INFORMATION: X at polition 10 may be any amino acid.
<220> FEATURE:
<221> NAME/KEY: MISC_FEATURE
<222> LOCATION: (11)..(11)
<223> OTHER INFORMATION: X at polition 11 is selected from L and I only.
```

```
<400> SEQUENCE: 28

Leu Xaa Xaa Leu Xaa Leu Xaa Xaa Asn Xaa Xaa
1               5                   10
```

MODIFIED PRO-α PEPTIDES AND THEIR USES

This application is the U.S. national phase under 35 U.S.C. § 371 of PCT International Application No. PCT/GB2004/001719, which has an International filing date of Apr. 21, 2004, designating the United States of America, and claims the benefit of British Patent Application No. 0309064.4, which was filed Apr. 22, 2003. The disclosures of each of these prior applications are hereby incorporated by reference herein.

The present invention relates to modified extracellular matrix molecules, to polymers, matrices and gels made therefrom and to their uses in such applications as wound healing.

There is a need for new clinical therapies to treat chronic wounds. The wound care market is vast and the cost to health authorities treating foot and leg ulcers is an estimated $7,000 million p.a. worldwide (FDA website http://www.fda.gov/). The existing treatments for such wounds include glutaraldehyde—cross-linked collagen implants, type I collagen gels containing cultured fibroblasts or fibroblasts supported on polyacid substrates. The use of chemical substrates, exogenous cells and crosslinking compounds increases the risk of implant rejection, antigenic responses and poor integration at the wound margin. Also, dressings containing pre-cultured cells are difficult to scale up and deliver fresh to the patient.

Furthermore, the standard treatment for chronic wounds, such as venous ulcers, is the use of absorbent or non-absorbent dressings in conjunction with compression therapy. However, this approach is only moderately effective, is uncomfortable for the patient, can take several months to take effect and recurrence occurs in the majority of cases where treatment is completed. Therefore, there is a an urgent need for the treatment and management of chronic wounds that avoids repeated applications of expensive dressings and which fail to address the underlying cellular and molecular mechanisms contributing to the pathogenesis of delayed healing. One of the most important contributing factors that results in the standard treatments for wound healing being only moderately effective is the markedly reduced deposition of collagen at the wound site associated with impaired cellular infiltration.

Most cells, whether simple unicellular organisms or cells from human tissue, are surrounded by an intricate network of macromolecules which is known as the extracellular matrix (ECM) and which is comprised of a variety of proteins and polysaccharides. A major protein component of the ECM is a family of related proteins called the collagens which are thought to constitute approximately 25% of total proteins in mammals. There are at least 26 genetically distinct types of collagen molecule, some of which are known as fibrillar collagens (collagen types I, II, III, V and XI) because they typically form large fibres, known as collagen fibrils, that may be many micrometers long and may be visualised by electron microscopy.

Collagen fibrils are comprised of polymers of collagen molecules and are produced by a process involving conversion of procollagen to collagen molecules that then assemble to form the polymer. Procollagen consists of a triple stranded helical domain in the centre of the molecule and has non-helical domains at the amino terminal (known as the N-terminal propeptide) and at the carboxyl terminal (known as the C-terminal propeptide). The triple stranded helical domain is made up of three polypeptides which are known as α chains. Procollagen is made intracellularly from pro-α chains (α chains with N and C-terminal forming propeptides domains). Pro-α chains are synthesised on membrane-bound ribosomes following which the pro-α chains are inserted into the endoplasmic reticulum. Within the endoplasmic reticulum the pro-α chains are assembled into a procollagen molecule. Procollagen is secreted into the extracellular environment where it is then converted into collagen by the action of procollagen N-proteinases (which cleave the N-terminal propeptide) and procollagen C-proteinases (which cleave the C-terminal propeptide). Once the propeptides have been removed the collagen molecules thus formed are able to self-assemble spontaneously to form the collagen fibrils. The rate determining step in the formation of collagen fibrils is the removal of the C-propeptides by procollagen C-proteinases.

Collagen fibrils interact with other fibrils and also other components of the extracellular matrix to form connective tissues in vivo. Fibrils will assemble in vitro and will interact to form a collagen matrix or gel. Such collagen matrices have various industrial uses. For instance, collagen-based biomedical products are used in the cosmetic and aesthetic enhancement markets as implants and for smoothing lines, wrinkles and facial scars. Collagen based products are also used in the production of artificial skins (e.g. for treating burns patients), wound dressings and the like.

Whilst collagen based products have been extensively adopted, their performance is far from satisfactory and a number of contra-indications and adverse reactions are known. Some of the problems are related to the fact that many of these products are based on animal collagen (e.g. from bovine hide) and as such can give rise to allergic and inflammatory-reactions and infections. Other collagen products are derived from cadaver tissue and it is suggested that they result in reduced inflammation and allergic reactions. However such products are expensive to manufacture and difficulties in controlling product quality can lead to variation in performance.

Another important function of the ECM is the storage and presentation of growth factors to cells. Proteoglycan components of the ECM play a central role in the regulation of the activity of a number of growth factors and therefore represent powerful pathophysiological modulators.

A well known example of a family of proteoglycans has a core protein of about 40 kDa that consists mainly of leucine-rich repeats of 20-24 amino acids. These proteins are known as Small Leucine-Rich Proteoglycans (SLRPs) and typically contain the sequence $LX_2LXLX_2NX(L/I)$ (Seq ID No. 29) where L=leucine; N=asparagines; I=isoleucine are in the specified conserved positions and X=any amino acid.

The SLRP family comprises at least 4 members, namely decorin, biglycan, fibromodulin and lumican (all of which were characterised in some detail in the late 1980s/early 1990s). These proteoglycans have specialised functions in cell cycle regulation, in tissue repair and in modulating the mechanical properties of tissues by their interaction with collagen fibrils. Decorin and related proteoglycans have also been reported to bind to and modulate the activity of various growth factors including members of the transforming growth factor β (TGF-β) family. Growth factors such as the TGF-βs have a major influence on cell activity and ECM remodelling. There are at least 5 different TGF-βs (TGF-β1-TGF-β5) and their chemical structures and activity have been widely reported (e.g. see Sporn et al. J. Cell Biol. 105: 1039 (1987).

A major pathophysiological activity of TGF-βs (particularly TGF-β1 and TGF-β2) is the promotion of wound healing. However this is often associated with increased scar formation and fibrosis. In fact, clinical interest in the modulation of TGF-β has been associated with inhibiting its activity in order to reduce scar formation (although this may compromise the rate of wound healing). For instance, WO 92/17206 discloses compositions which inhibit the activity of TGF-β1 and TGF-β2 and are particularly beneficial for reducing scar formation.

Another proteoglycan that is known to bind to TGF-βs is the type III TGF-β receptor. This proteoglycan is a cell membrane receptor that can act as a reservoir for TGF-β and is also known as betaglycan (or soluble betaglycan if cleaved from the cell membrane and found free in the ECM).

The modulation of the activity of growth factors such as TGF-β is of significant clinical interest. Various parties have investigated the usefulness of proteoglycans as pharmacologically active agents. For instance, the use of such molecules to regulate fibrotic conditions, wound healing and scarring is contemplated in:

(1) WO 93/09800—relating to the use of decorin and related proteoglycans as agents for preventing or reducing scarring; and (2) WO 97/05892—which discloses the use of soluble betaglycan as an anti-scarring agent The Applicant's co-pending application No. PCT/GB2002/004785 relates to novel modified procollagen molecules wherein at least one N-terminal domain of the molecule contains a polypeptide sequence from at least part of a proteoglycan protein core. The production of collagen gels and matrices from such modified procollagens has been found to assist in wound healing by attracting growth factors to the wound site. Furthermore, the procollagen matrices have been found to have increased resistance to cell shrinkage.

Despite these advances there remains a need to develop further medicaments for assisting in wound healing whilst avoiding or reducing the drawbacks experienced with the prior art applications.

Laminins are a large family of multifunctional glycoproteins which are distributed ubiquitously within basement membranes. The laminins have key roles in development, differentiation and migration due to their ability to interact with cells by means of their high affinity binding sites via cell-surface reactors including integrins and type IV collagen. They are composed of three genetically distinct chains, being αβγ heterotrimeric proteins that assemble into a cruciform molecule with one long arm and three short arms. There are 18 different laminin isoforms, including Laminin-1, Laminin-2, Laminin-5 and Laminin-10.

The laminins are known to bind keratinocytes and provide survival and differentiation signals to epithelial cells and keratinocytes which are critical cells needed for re-epithelialisation of dermal wounds.

A further molecule that is secreted into the extracellular matrix and is involved in wound healing is secretory leukocyte protease inhibitor (SLPI). This molecule, also known as antileukoprotease, is an 11.7 kD cationic inhibitor of neutrophil elastase. In addition to protecting against injury, it has also been shown that it functions as an antimicrobial and anti inflammatory. SLPI is produced naturally by the blood and modifies levels of elastase, a substance which breaks down the skin.

It is an object of the present invention to address problems associated with prior art medicaments and delivery systems. A farther object of the present invention is to address problems associated with collagen matrices and gels known in the art.

The present invention is based upon the realisation by the inventors that desirable functional characteristics may be introduced into a composition such as a medicament or collagen matrix by designing modified pro-α chains according to a first aspect of the present invention which may be trimerised to form procollagen derivatives. These in turn may be converted to collagen monomers (with retained propeptides) and subsequently polymerised. This allows the synthesis and assembly of novel collagen polymers having new biological properties.

To this end, a first aspect of the present invention provides a modified pro-α chain comprising a triple helical forming domain linked to at least an N-terminal domain characterised in that the N-terminal domain contains a polypeptide sequence from at least part of a laminin glycoprotein or at least part of a secretory leukocyte protease inhibitor or functional derivatives thereof.

The inventors have found that they can employ molecular biology techniques to modify the gene encoding pro-α chains such that modified pro-α chains according to the first aspect of the invention may be expressed therefrom. Therefore according to a second aspect of the invention there is provided a DNA molecule encoding modified pro-α chains according to the first aspect of the invention.

The inventors then trimerised modified pro-α chains according to the first aspect of the invention to form a procollagen molecule with a modified N propeptide. The trimer may be a homotrimer of modified pro-α chains or may be a heterotrimer also containing natural pro-α chains. Therefore according to a third aspect of the present invention there is provided a procollagen molecule comprising a trimer of pro-α chains characterised in that at least one of the pro-α chains is a pro-α chain according to the first aspect of the invention.

The inventors then performed further experiments that established that procollagen molecules according to the third aspect of the invention may be polymerised to form a collagen polymer. Furthermore they have established that they can regulate N-propeptide cleavage by modifying the N-terminal domain such that the domain's susceptibility to cleavage is altered such that the collagen polymer retains N-propeptides or derivatives thereof upon its surface. This may be achieved by designing procollagen molecules according to the third aspect of the invention such that they are resistant to procollagen N-proteinases. Alternatively, the molecules may only be partially cleaved or cleaved more slowly. It is preferred that pro-α chains according to the first aspect of the invention are also modified such that they contain an amino acid sequence that confers resistance to procollagen N-proteinases.

Alternatively the inventors have found that they can assemble collagen polymers with retained N-propeptides in an environment in which procollagen N-proteinase is either inhibited or absent.

According to a fourth aspect of the invention there is provided a collagen polymer with at least some of the collagen monomers contained therein having retained N-terminal ends characterised in that at least some of the retained N-terminal ends contain a polypeptide sequence encoding at least part of a laminin glycoprotein, at least part of a secretory leukocyte protease inhibitor or functional derivatives thereof.

Collagen polymers according to the fourth aspect of the invention may form collagen fibrils.

Additionally, the C-terminal domains of the procollagens making up the collagen polymer may be removed, for example using a procollagen C-proteinase, such as bone morphogenetic protein (BMP-1). This has been found to result in the N-terminal propeptides being presented at the fibril surface.

EP-A-0 985 732 contemplates the production of chimeric collagens with biologically active peptides (e.g. a growth factor per se) fused to the N-terminal and which can polymerise to form fibrils. However BP-A-0 985.732 does not contemplate or suggest the addition of the polypeptide sequence of at least part of a laminin or secretory leukocyte protease inhibitor (SLPI) to the N terminal domain of a pro-α chain according to the first aspect of the invention.

Modified pro-α chains according to the first aspect of the invention are preferably modified forms of fibrillar forming procollagens (e.g. modified forms of type I, II, III, V or XI pro-α chains). Preferably the molecule is a modified type III pro-α chain. This type is preferred because it can coassemble with type I collagen and can also form a homotrimer. It is most preferably a modified proα1(III) chain.

It is prefered that only part of a laminin molecule is attached to the pro-α chain. More preferably, the N-terminal ends are derived from the globular domains of an α-chain of a laminin molecule. It is most preferred that the N-terminal end comprises the amino acid sequence for at least the G3 globular domain of the α-chain. Alternatively, the N-terminal may comprise the amino acid sequence for the G1 to G3 domains.

In a preferred embodiment of the invention, the N-terminal sequence of the pro-α chain is replaced with at least part of the amino acid sequence of the α3-chain of Laminin-5 since Laminin-5 has a high affinity for cells of epithelial origin.

In the case of the replacement of the N-terminal end with the polypeptide sequence encoding at least part of a secretory leukocyte protease inhibitor, it is preferred that the entire sequence of the inhibitor is attached to the N-terminal domain.

Preferably, the N-propeptide sequence of the pro-α chain replaces the procollagen N-propeptide sequence prior to N100 to ensure that the collagen retains its signal sequence.

Natural N-terminal propeptide forming domains may be modified such that essentially all of the N-terminal end is replaced by a laminin glycoprotein or SLPI. The extent to which the normal N-terminal propeptide forming domain is replaced is less critical than ensuring that keratinocyte-binding functionality of the laminin molecule or the elastase inhibitory functionality of the SLPI molecule is introduced. Accordingly the N-terminal propeptide forming domain may be totally replaced, partially replaced or even maintained in its entirety (provided it has the required functionality added).

It is desirable to make some modified pro-α chains according to the present invention that trimerise to form procollagens that are resistant to N propeptide cleavage. Therefore some preferred molecules according to the first aspect of the invention have amino acid sequences defining a modified N-proteinase cleavage site which renders procollagens resistant to such cleavage. People with the Ehlers Danlos syndrome type VII have mutations in a collagen gene which abolishes the N-proteinase cleavage site on the procollagen molecule. Therefore with knowledge of this mutation the region of the domain requiring such modification is easily identified.

The region between the helical forming domain and N-propeptide forming domain of the pro-α chain (the so called hinge domain) is most suitably modified to confer resistance to N-proteinases. For instance, Pro-Gln at the cleavage site may be altered to Leu-Pro.

Modified pro-α chains according to the first aspect of the invention may be formed by direct chemical synthesis or by in vitro amino acid polymerization followed by protein folding and, if appropriate, glycosylation of the modified polypeptide sequence. However it is preferred that molecular biology techniques are used to design a DNA molecule according to the second aspect of the invention and express the modified pro-α chain in a cell or expression system containing such a DNA molecule.

The DNA molecule according to the second aspect of the invention may be formed by manipulating the bases encoding the N-terminal propeptide forming domains such that amino acids are added, substituted or deleted. It is preferred that a nucleotide sequence encoding a laminin, SLPI or functional derivatives thereof is inserted into the bases encoding the N propeptide forming domain. It is particularly preferred that a nucleotide sequence encoding at least the G3 domain of the α-chain of a laminin glycoprotein or all of the SLPI molecule is inserted into the bases encoding the N propeptide forming domain.

Preferred modifications include the insertion of a nucleotide sequence encoding the G3 or the G1, G2 and G3 domains of the u-3 chain of Laminin-5.

Alternatively the, bases encoding an N propeptide forming domain of a natural pro-α chain may be completely excised and replaced with bases encoding at least one of the globular domains of an α-chain of laminin or those encoding the SLPI molecule.

According to a preferred embodiment of the invention, the DNA molecule may encode a C-propeptide domain and an α-chain of a pro-αchain and may have the "natural" N-propeptide entirely replaced by a sequence encoding at least one globular domain of an α-chain of a laminin glycoprotein or the SLPI protein.

As previously indicated it is desirable to make some pro-α chains, procollagens or collagen polymers according to the present invention resistant to N propeptide cleavage. Therefore some preferred DNA molecules according to the second aspect of the invention have DNA sequences encoding a modified N-proteinase cleavage site which alters the proteins expressed therefrom resistance to such cleavage. Preferably, the expressed proteins are resistant to cleavage. Alternatively, cleavage in the expressed protein may be partial or slower than in the un-modified protein. It is preferred that the region between the helical forming domain and N-propetide forming domain of the pro-α chain (the so called hinge domain) is mutated to confer resistance to N-proteinases. For instance, nucleotides encoding Pro-Gln at the cleavage site may be altered to nucleotides encoding Leu-Pro.

The DNA molecule may be incorporated within a suitable vector to form a recombinant vector. The vector may for example be a plasmid, cosmid or phage. Such vectors will frequently include one or more selectable markers to enable selection of cells transfected with the said vector and, preferably, to enable selection of cells harbouring the recombinant vectors that incorporate the DNA molecule according to the second aspect of the invention.

Standard molecular biology techniques may be used to construct vectors comprising DNA molecules according to the second aspect of the invention. Preferred constructs and expression systems are described in more detail in the Examples.

Vectors may be expression vectors and have regulatory sequences to drive expression of the DNA molecule. Vectors not including such regulatory sequences may also be used and are useful as cloning vectors for the purposes of replicating the DNA molecule. When such vectors are used the DNA molecule will ultimately be required to be transferred to a suitable expression vector which may be used for production of the procollagen derivative of the invention.

Replication of the DNA molecule in cloning vectors or expression of the protein product from recombinant expression vectors is performed within a suitable host cell. The DNA molecule may be incorporated within a vector within the host cell. Such host cells may be prokaryotic or eukaryotic. Eulkaryotic hosts may include yeasts, insect and mammalian cells. Hosts used for expression of the protein encoded by the DNA molecule are ideally stably transformed, although the use of unstably transformed (transient) hosts is not precluded.

A preferred host cell is the HEK293 cell line and derivatives thereof.

The DNA molecule of the invention may also be incorporated in a transgene construct designed for expression in a transgenic plant or, preferably, animal. Transgenic animals which may be suitably formed for expression of such transgene constructs, include birds such as domestic fowl, amphibian species and fish species. The protein may be harvested from body fluids or other body products (such as eggs, where appropriate). Preferred transgenic animals are (non-human) mammals, particularly placental mammals. An expression product of the DNA molecule of the second aspect of the invention may be expressed in the mammary gland of such mammals and the expression product may subsequently be recovered from the milk. Ungulates, particularly economically important ungulates such as cattle, sheep, goats, water buffalo, camels and pigs are most suitable placental mammals for use as transgenic animals according to the invention. The generation and usefulness of such mammalian transgenic mammary expression systems is both generally, and in certain instances specifically, disclosed in WO-A-8800239 and WO-9005188.

It is preferred that the host contains suitable intracellular facilities for the assembly of the procollagen derivative of the first aspect of the invention from the protein products of the DNA molecule of the second aspect of the invention. In particular, expression hosts, particularly transgenic animals, may contain other exogenous DNA the expression of which facilitates the expression, assembly, secretion or other aspects of the biosynthesis of procollagen derivatives of the third aspect of the invention and even collagen polymers according to the fourth aspect of the invention. For example, expression hosts may co-express prolyl 4-hydroxylase, which is a post translation enzyme important in the natural biosynthesis of procollagens, as disclosed in WO-9307889.

DNA, particularly cDNA, encoding natural pro-α chains is known and available in the art. For example, WO-A-9307889, WO-A-9416570 and the references cited in both of them give details. Such DNA may be used as a convenient starting point for making a DNA molecule of the present invention. Recombinant techniques may be used to derive the DNA molecule of the invention from such a starting point.

DNA sequences, cDNAs, full genomic sequences and minigenes (genomic sequences containing some, but not all, of the introns present in the full length gene) may be inserted by recombinant means into a DNA sequence coding for naturally occurring pro-α chains (such as the starting point DNA mentioned above) to form the DNA molecule according to the second aspect of the invention. Because of the large number of introns present in collagen genes in general, experimental practicalities will usually favour the use of cDNAs or, in some circumstances, minigenes. The inserted DNA sequences, cDNAs, fall genomic sequences or minigenes code for amino acids which when expressed and assembled into a procollagen according to the third aspect of the invention give rise to a desired modification in the N-terminal domain of such a procollagen derivative.

Any of the DNA material used in these methods (including the DNA sequences, cDNAs, full genomic sequences and minigenes; the DNA molecule according to the second aspect of the invention and vectors) may be prepared by any convenient method involving coupling together successive nucleotides, and/or ligating oligo- and/or poly-nucleotides, including in vitro processes. However recombinant DNA technology forms the method of choice.

A preferred vector for DNA molecules according to the second aspect of the invention is the episomally replicating plasmid pCep4. This plasmid allows high levels of expression of cloned DNA molecules in cell-lines such as HEK293 transfected with the EBV nuclear antigen.

Collagen polymers in accordance with the fourth aspect of the invention may be of a number of forms. Cylindrical polymers similar to collagen fibrils are generated from mixtures of collagen molecules and collagens derived from procollagens according to the third aspect of the invention when collagen molecules are the major component. Alternatively, sheet-like structures may be formed by using procollagen derivatives according to the third aspect of the invention in the absence of, or substantially in the absence of, normal collagen molecules.

A remarkable feature of collagen polymers according to the fourth aspect of the invention is that the modified N-terminal propeptides are located to the surface of the polymer/fibril so formed, particularly in the case where the C-terminal domain of the procollagen has been removed. The inventors have demonstrated that fibrils formed from mixtures of natural collagens and modified procollagens according to the third aspect of the invention exhibit the modified N-propeptides at the fibril surface whereas the natural collagens (i.e. those without retained N-propeptides) form the core of the fibril. The arrangement of the molecules in the fibril optimises presentation of the N-propeptides to the interfibrillar space.

Additionally, the inventors were able to form collagen matrices from procollagen molecules according to the third aspect of the invention and/or collagen polymers according to the fourth aspect of the invention. Said collagen matrices form an important fifth aspect of the invention.

Preferably, the matrix is characterised by the fact that at least some of the collagen monomers have a N terminal domain containing at least part of a laminin glycoprotein or at least part of a secretory leukocyte protease inhibitor.

The collagen matrices according to the fifth aspect of the invention have several advantages over known collagen matrices. The incorporation of the globular domain of a laminin glycoprotein into the collagen matrix promotes keratinocyte crawling due to their keratinocyte binding properties and thereby accelerate re-epithelialisation. Thus, the matrices may be used to recruit viable cells from wound margins.

Furthermore, the incorporation of SLPI domain into the collagen matrices also aids wound healing, provides antimicrobial and antiflammatory properties and reduces breakdown of the skin.

Collagen matrices according to the fifth aspect of the invention are preferably made from human recombinant DNA molecules according to the second aspect of the invention. When this is the case, a third advantage is that the matrices are less likely to cause allergic and inflammatory responses when administered to humans.

A collagen matrix may be formed by neutralising and warming acidic solutions of collagen monomers or procollagens (in the presence of suitable proteinases). Under such conditions the collagen monomers spontaneously self-assemble into polymeric fibrils that then become entangled to form a hydrated and porous gel. The rigidity of such a gel is, at least in part, dependent on the concentration of the collagen used to form the gel and on the diameter of the collagen fibrils formed. The collagen matrix or gel assumes the shape of the container in which it is formed. Therefore, gels can be made that are thin (millimetres) in one dimension and extensive (centimetres or larger) in other dimensions. Such matrices can be suitably shaped to form the basis of replacement skin or cornea. Alternatively, collagen gels can be cast in moulds that have the shape of long bones (cylindrical and long), jaw bones (sickle shaped or curved), articular cartilage (disc shaped), tendon (rope shaped) or ligament (shaped like a strap).

Collagen polymers and matrices according to the fourth and fifth aspects of the invention may comprise exclusively recombinant collagen derived from modified procollagen molecules according to the invention. Alternatively such collagen polymers or matrices may be mixtures of modified collagens or modified procollagens according to the invention and collagen extracted from tissue or cell cultures, such as is available from commercial sources. For example, collagen polymers according to the fourth aspect of the invention may be combined with bovine type I collagen to form a matrix according to a fifth aspect of the invention.

Procollagens or collagens according to the present invention may be used to coat the surfaces of collagen fibrils in a gel or matrix formed from natural collagens (e.g bovine collagens) or they may be incorporated into the fibrils during gel formation. The new functional moieties introduced into the procollagens or collagens are thereby presented to the surface of the collagen fibrils where they can interact with cells or influence cellular function. The procollagens may be applied as a soluble precursor with a procollagen C-proteinase such as BMP-1 which converts the soluble procollagen to fibril-forming collagen having its N-terminal domain retained to allow gel formation in situ. This enables the modified collagen to integrate and mesh with collagen fibrils at the point of application.

Molecules according to the first-fifth aspects of the invention may be employed in a research setting for exploring a wide range of biological phenomenon from cell adhesion to wound healing and from cell differentiation and apoptosis to the manufacture of wound dressings with improved molecule and cell binding properties. However, a preferred use of the molecules is in the formation of collagen matrices which may be used for medical or cosmetic purposes.

According to a sixth aspect of the present invention there is provided the use of a molecule or matrix according to any one of the first-fifth aspects of the invention for the treatment of medical conditions.

According to a seventh aspect of the present invention there is provided the use of a molecule or matrix according to any one of the first-fifth aspects of the invention for the manufacture of a medicament for use in the treatment of wounds or fibrotic disorders.

According to a eighth aspect of the present invention there is provided a method of treating wounds comprising administering to a subject in need of treatment a therapeutically effective amount of a molecule or matrix according to any one of the first-fifth aspects of the invention.

It is preferred that the medical conditions treated are conditions that are at least partially characterised by remodelling of the ECM.

Whilst the above considerations mainly apply to conditions, disorders or diseases of man it will be appreciated that wound healing can also be problematic in other animals, particularly veterinary or domestic animals (e.g. horses, cattle, dogs, cats etc). For instance abdominal wounds or adhesions are a major reason for having to put down horses (particularly race horses), as are tendon and ligament damage leading to scarring or fibrosis.

Molecules according to the third and fourth aspects of the invention and a matrix according to the fifth aspect of the invention may be formulated into a various types of medicament. The medicament of the invention may take a number of different forms depending, in particular on the manner in which the medicament is to be used. Thus, for example, the medicament may be in the form of a liquid, ointment, cream, gel, hydrogel, powder, aerosol or an implantable device (e.g. by conjugation to a biopolymer sponge).

Molecules according to the third and fourth aspects of the invention may be administered directly (e.g. in liquid form). However, it is preferred that the molecules are incorporated into a wound dressing, an implantable device, artificial skin or tissue etc.

It is preferred that the medicaments are for topical application. The medicament may be most suitably used for topical application to the skin or wound area.

Medicaments comprising modified procollagens, collagens or collagen fibrils may be delivered by means of an aerosol (e.g. for delivery to fibrotic conditions of the lung).

It will be appreciated that the vehicle of the medicament should be one which is well tolerated by the patient and allows release of the collagen polymer to the wound or site of fibrosis. The vehicle will ideally be sterile and may be combined with excipients and/or stabilizers as well as the molecule to form the medicament. Such a vehicle is preferably biodegradeable, bioresolvable, bioresorbable and/or non-inflammatory.

The medicament may be used in a number of ways. Thus, for example, it may be applied in, and/or around a wound of a patient to provide the desired promotion of wound healing. If the composition is to be applied to an "existing" wound, then the pharmaceutically acceptable vehicle will be "mild" enough such that it does not cause an inflammatory response or is toxic to the tissue. Clearly, the inclusion of modified collagen containing the SLPI molecule will assist in reducing any inflammatory response.

Molecules according to the third or fourth aspects of the invention may be provided on a sterile dressing or patch which may be used to cover or even pack a wound or fibrotic site.

The medicament may be provided as an implantable device from which it may be released better. For instance, it may be released by biological dissolution or degradation of the device. Alternatively an external stimulus, such as ultrasound, may cause release of the procollagen, collagen monomer or collagen polymer.

It is also possible to use medicaments in accordance with the invention in a prophylactic manner. For instance, the medicament may be applied prior to surgery so as to provide for regulation of healing of the subsequently formed surgical wound.

A collagen matrix may then be administered to a subject (e.g. to the skin, cartilage, muscle or neural tissues) in the form of a semi-solid gel. Alternatively a more solid matrix may be formed which may be used in the formation of a wound dressing, an implantable device, artificial skin or tissue etc.

Artificial skins comprising matrices according to the fifth aspect of the invention may comprise ECM components alone or may further comprise cultured cells such as fibroblasts and/or endothelial cells. Artificial skins containing such cells are known as "living" replacement skin products.

It is preferred that the collagen matrices are formed into artificial skin for topical application to dermal wounds or burns. The artificial skins comprising matrices according to the fifth aspect of the invention are particularly useful for treating severe wounds, extensive wounds, chronic wounds (e.g. dermal ulcers) and burns.

It will be appreciated that the matrix should be hydrated in a pharmaceutically acceptable vehicle. The vehicle should be sterile and "mild" enough such that it does not cause an inflammatory response or is toxic to the tissue being treated.

The matrix may be incorporated into a sterile dressing or patch which may be used to cover or even pack a wound or fibrotic site.

In a preferred embodiment, the matrix is applied to a dressing, such as a Combiderm N dressing and then dehydrated. The dehydrated gel carried on the dressing is then applied to a wound.

The matrix may be provided as an implantable device from which the matrix per se may be released into the wound site. Release may be caused by biological dissolution or degradation of the device. Alternatively an external stimulus, such as ultrasound, may cause release of the collagen polymer.

A collagen matrix according to the fifth aspect of the invention may be cast into a sheet. Preferred sheets may be 1—several millimetres thick by several centimetres square. Such sheets can be acellular or populated with mesenchymal and/or fibroblastic cells to generate an artificial skin, cartilage, bone or cornea, or endothelial cells to produce cardiovascular patches. The cells may be obtained from a patient or a tissue-matched donor, stem cells from a patient or a donor, or cells that have been amplified in culture. Such matrices may be coated with molecules according to the third and fourth aspects of the invention to confer keratinocyte binding functionality or elastase inhibition to the matrix. The collagen matrix or collagen-cell construct can be stored under aseptic conditions and at physiological temperatures or under cryogenic storage conditions until needed.

It will be appreciated that the amount of molecule required to modulate healing and fibrosis depends on a number of factors such as its biological activity and bioavailability, which in turn depends on the mode of administration and the physicochemical properties of the particular molecule used. For example, the amount of collagen matrix required will depend upon factors such as the concentration of the gel (this may be required to be aqueous, viscous or relatively solid—depending upon the clinical need) and the proportion of collagens with the new functional moieties contained therein. Other factors include:

A) The specific condition to be treated.
B) The severity of the condition.
C) The age of the subject.
D) The site of delivery.
E) The half-life of the molecule in the subject being treated.

The frequency of administration will also be influenced by the above mentioned factors and particularly the half-life of the compound or matrix within the subject being treated.

Generally, a subject being treated will derive benefit from the application of the modified procollagen, collagen monomer or collagen polymer, if as administered to a wound within 7 days of wounding, preferably within 48 hours of wounding, more preferably within 24 hours of wounding and even more preferably within 12 hours of wounding. The medicament should be administered to a subject suffering from a fibrotic condition according to a clinicians directions. This may be as soon as diagnosis has occurred. Therapy should continue until the wound has healed or fibrotic disorder cleared to a clinicians satisfaction.

When used as a prophylactic (e.g. before surgery) the medicament should be administered as soon as it is recognised that a wound may occur or fibrotic disorder may develop. For instance, a cream or ointment containing collagen polymer according to a fourth aspect of the invention may be applied to a site on the skin of a subject where elective surgery is to be performed and an increased rate of wound healing is subsequently desired. In this case, the medicament may be applied during the preoperative preparation of the subject or it may even be desirable to apply it in the hours or days preceding the surgery (depending upon the health status and age of subject as well as the size of the wound to be formed).

Frequency of administration will depend upon the biological half-life of the molecule used. Typically a cream or ointment should be administered to a target tissue such that the concentration of the molecule at the wound site is maintained at a level suitable for having a therapeutic effect. This may require administration daily or even several times daily.

Known procedures, such as those conventionally employed by the pharmaceutical industry (e.g. in vivo experimentation, clinical trials etc), may be used to establish specific formulations of compositions and precise therapeutic regimes (such as daily doses of the compounds and the frequency of administration).

Generally, for use in accordance with the invention a medicament containing an amount of 1 ng to 1 mg of collagen polymer, more preferably 1 µg to 1 mg of collagen polymer, may be applied per centimetre of linear wound. Purely by way of example, a medicament containing about 10 µg collagen polymer is suitable for application to a 1 cm linear incisonal wound. Higher doses are required to stimulate the healing of chronic wounds compared to acute wounds.

Efficacy of medicaments, and particularly those formulated for application to chronic wounds, have enhanced efficacy when combined with a protease inhibitor (e.g. galadrin) Protease inhibitors prevent or retard the degradation of the collagen by proteases which may be found in high levels in wounds, particularly chronic wounds. The protease inhibitor is preferably a broad spectrum protease inhibitor.

It will be appreciated that the molecules and matrices according to the third, fourth and fifth aspects of the invention may be used in combination with other wound healing or anti-fibrotic agents or followed by another agent (e.g. for prevention of scarring).

It will be appreciated that matrices according to the fifth aspect of the invention (used to treat medical conditions, cosmetically or otherwise) may be formed in situ (i.e. at the tissue/site where the matrix is required). For instance, a solution or slurry of collagen polymers according to the fourth aspect of the invention may be used to soak a wound dressing. Gel formation may be induced when the dressing is used (e.g. a reaction may initiated when the dressing is removed from its package or contacts a wound site). Alternatively a solution of collagen polymers according to the fourth aspect of the invention, or even procollagens according to the third aspect of the invention may be injected into a target body tissue and matrix formation allowed to proceed with native collagens.

DNA molecules according to the second aspect of the invention may be used in gene therapy techniques. Therefore according to a ninth aspect of the present invention there is provided a delivery system for use in a gene therapy technique, said delivery system comprising a DNA molecule according to the second aspect of the invention which is capable of being transcribed to lead to the expression of a modified pro-α chain according to the first aspect of the invention at a wound site or site of fibrosis.

According to a tenth aspect of the present invention there is provided the use of a delivery system as defined in the preceding paragraph for use in the manufacture of a medicament for treating wounds or fibrotic disorders.

According to an eleventh aspect of the present invention there is provided a method of treating a wound or fibrotic condition which consists of administering to a patient in need of treatment a therapeutic dose of a delivery system as defined above.

The delivery systems are highly suitable for achieving sustained levels of a procollagen molecule according to the third aspect of the invention or a collagen polymer according to the fourth aspect of the invention at a wound site or site of fibrosis over a longer period of time than is possible for most conventional delivery systems. Modified pro-α chains may be continuously expressed from cells at the site that have been transformed with the DNA molecule of the second aspect of the invention. Therefore, even if the modified procollagen or collagen polymer has a very short half-life as an agent in vivo, therapeutic doses may be continuously expressed from the treated tissue.

Furthermore, the delivery system of the invention may be used to provide the DNA molecule without the need to use conventional pharmaceutical vehicles such as those required in ointments or creams that are contacted with the wound or site of fibrosis. This is particularly beneficial as it can often be difficult to provide a satisfactory vehicle for a compound for use in wound healing (which are required to be non-inflammatory, biocompatible, bioresorbable and must not degrade or inactivate the active agent (in storage or in use)).

The delivery system is such that the DNA molecule is capable of being expressed (when the delivery system is administered to a patient) to produce modified pro-α chains which form procollagens and then collagen polymers with the modified N terminals. These modified N terminals then interact with cells or biologically active agents at the site of the wound or fibrosis and thereby treat the condition.

The DNA molecule may be contained within a suitable vector to form a recombinant vector. The vector may for example be a plasmid, cosmid or phage. Such recombinant vectors are highly useful in the delivery systems of the invention for transforming cells with the DNA molecule. The vector may be pCEP4 or a similar vector.

Recombinant vectors may also include other functional elements. For instance, recombinant vectors can be designed such that the vector will autonomously replicate in the nucleus of the cell. In this case, elements which induce DNA replication may be required in the recombinant vector. Alternatively the recombinant vector may be designed such that the vector and recombinant DNA molecule integrates into the genome of a cell. In this case DNA sequences which favour targeted integration (e.g. by homologous recombination) are desirable. Recombinant vectors may also have DNA coding for genes that may be used as selectable markers in the cloning process.

The recombinant vector may also further comprise a promoter or regulator to control expression of the gene as required.

The DNA molecule may (but not necessarily) be one which becomes incorporated in the DNA of cells of the subject being treated. Undifferentiated cells may be stably transformed leading to the production of genetically modified daughter cells (in which case regulation of expression in the subject may be required e.g. with specific transcription factors or gene activators). Alternatively, the delivery system may be designed to favour unstable or transient transformation of differentiated cells in the subject being treated. When this is the case, regulation of expression may be less important because expression of the DNA molecule will stop when the transformed cells die or stop expressing the protein (ideally when the wound, fibrosis or scarring has been treated or prevented).

The delivery system may provide the DNA molecule to the subject without it being incorporated in a vector. For instance, the DNA molecule may be incorporated within a liposome or virus particle. Alternatively the "naked" DNA molecule may be inserted into a subject's cells by a suitable means e.g. direct endocytotic uptake.

The DNA molecule may be transferred to the cells of a subject to be treated by transfection, infection, microinjection, cell fusion, protoplast fusion or ballistic bombardment. For example, transfer may be by ballistic transfection with coated gold particles, liposomes containing the DNA molecule, viral vectors (e.g. adenovirus) and means of providing direct DNA uptake (e.g. endocytosis) by application of plasmid DNA directly to the wounded area topically or by injection.

Whilst the above considerations mainly apply to wounds of man it will be appreciated that wound healing, can also be problematic in other animals (especially veterinary and domestic animals such as cattle, horses, dogs, cats etc). For instance, abdominal wounds or adhesions are a major reason for having to put down horses. The medicaments and delivery systems discussed above are also suitable for use in the healing of such animals.

The present invention will now be further described with reference to the following non-limiting examples and figures in which:

FIG. 1 schematically illustrates a natural procollagen molecule;

FIG. 2 schematically illustrates lam-procollagen, a procollagen molecule according to the third aspect of the invention;

FIG. 3 illustrates the nucleotide sequence of a DNA molecule according to the second aspect of the invention from Example 1;

FIG. 4 illustrates the amino acid sequence of a modified pro-α chain according to the first aspect of the invention from Example 1;

FIG. 6 illustrates the nucleotide sequence of a DNA molecule according to the second aspect of the present invention from Example 2;

FIG. 7 illustrates the amino acid sequence of a modified prove chain according to a first aspect of the invention from Example 2;

FIG. 8 illustrates the nucleotide sequence of a DNA molecule according to the second aspect of the invention from Example 3;

FIG. 9 illustrates the amino acid sequence of a modified pro-α chain according to the first aspect of the invention from Example 3.

Figure 1:
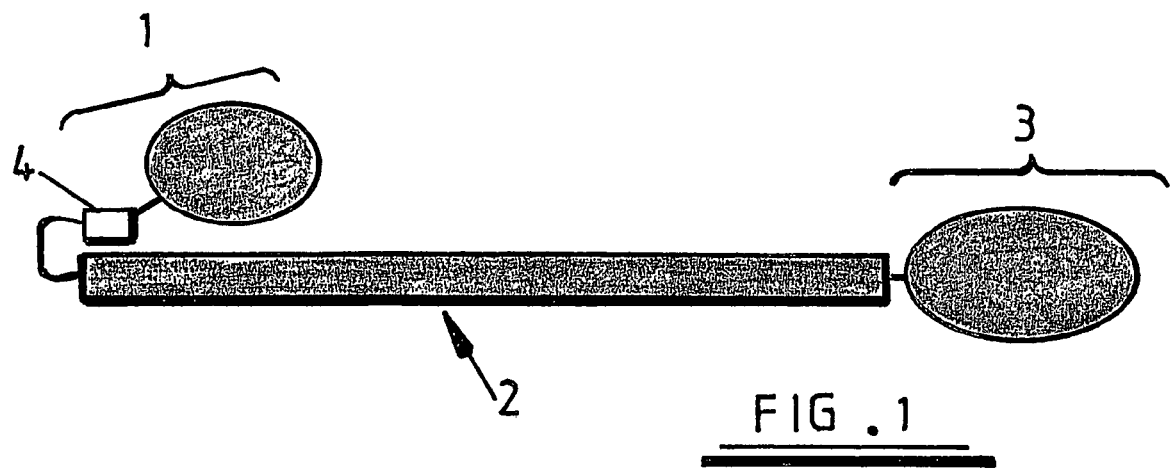
Figure 2:
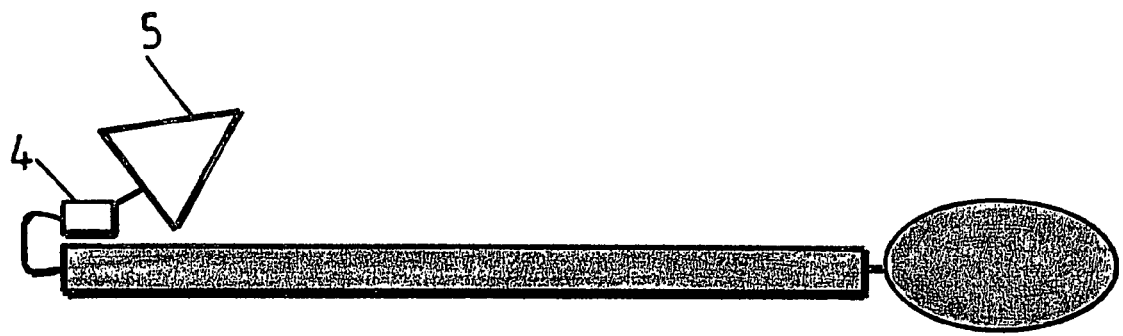

FIG. 1 illustrates a natural procollagen with an N-terminal propeptide 1, alpha helical domain 2 and a C-terminal propeptide 3. A procollagen N-Proteinase cleavage site 4 in the hinge region of the molecule (between 1 and 2) is also illustrated. FIG. 2 illustrates lam-proα1(III) or Lam-Coll™ a procollagen molecule according to the third aspect of the invention in which the N propeptide 1 has been replaced by at least one globular binding domain of laminin 5.

EXAMPLE 1

Design and Construction of a DNA Molecule According to the Second Aspect of the Invention, the Amino Acid Sequence of the Modified Pro-α Chain Expressed therefrom According to a First Aspect of the Invention and the Expression and Characterisation of Modified Procollagens Prepared therefrom According to a Third Aspect of the Invention A DNA molecule according to the second aspect of the invention was constructed comprising the entire coding region for the G1, G2 and G3 domains of the α-3 chain of Laminin 5 in place of the globular domain of the N-propeptide of the proα1(III) chain.

The cloning strategy for production of the DNA molecule involved the following primary PCR reactions.
1. Substrate: pRMI containing the complete cDNA for pro-α1(III) chain of collagen (publicly available X 14420).
   Oligonucleotides:

```
T3 (5' end)                       (Seq ID. NO:1)
5' AATTAACCCTCACTAAAGGG 3'

SSG1-20R (3' end)                 (Seq ID NO:2)
5' ACAGAGATGTTGCCAAAATAATAGTGGGATG 3'
```

Product A: 300 bp.
2. Substrate: Lam5α3-pSECTAG2C containing gene for α3 chain cloned in on Asp718I site
   Oligonucleotides:

```
SSG1-20F(5' end)                  (Seq. ID NO:3)
5' TATTTTGGCAACATCTCTGTCCTTGTTTCTC 3'

LG3-20R (3' end)                  (Seq. ID NO:4)
5' CTTGACCATTAGCATCTTGCCACACCTTCAC 3'
```

Product B: 1800 bp
3. Substate: pRM1
   Oligonucleotides:

```
LG3-20F (5' end)                  (Seq ID NO:5)
5' GCAAGATGCTAATGGTCAAGGACCTCAAGGC 3'

III-JL11 (3' end)                 (Seq ID NO:6)
5' AGACCCTGCAGGTCCAACTT 3'
```

Product C: 700 bp.

The following secondary PCR Reactions were then carried out.

1) Substrate: Mixture of A (300 bp) and (B(1.8 kb) products
   Oligonucleotides: T3 (5'end) LG3-20R (3'end)
   Product AB: 2.1 kb
2) Substrate: Mixture of B (1.8 kb) and C(700 bp)
   Oligonucleotides: SSG1-20F (5'end) III-JL11 (3'end)
   Product BC: 2.5 kb Cloning of AB and BC Products into pBluescript Product AB was digested with HindIII and Not1 and then ligated into pBS also digested with HindIII and Not1 to generate G123AB-pBS plasmid. Product BC was digested with HindIII and BAMH1 and then ligated into pBS also digested with HindIII and BAMH1 to generate G123BC-pBS plasmid.

Generation of Chimeric LamG123-Collagen Gene

The G123AB-pBS plasmid was digested with Not1 and HindIII and the 1.27 kb fragment was gel purified. The G123BC-pBS plasmid was digested with BamH1 and HindIII and the 1.36 kb fragment was gel purified. The pRMI plasmid was digested with Not1 and BamH1 and the 6.8 kb fragment was gel purified.

The three fragments were ligated together to generate the gene encoding the LamG123-collagen fusion protein. Correct assembly of the lamG123-collagen gene was determined by DNA sequencing.

Modification of the LamG123-Collagen/pBluescript Plasmid

A NotI site was introduced 3' to the collagen sequence by standard PCR mediated site-directed mutagenesis using the oligonucleotides TAS14NotA and Oligo32merTAS12NotS, details of which are as follows:

```
TAS14NotA (antisense)             (Seq ID NO:7)
5' GTTGTAAAACGGCGGCCGCTGAATTGTAATAC 3'

Oligo32merTAS12NotS (sense)       (Seq ID NO:8)
5' GTATTACAATTCAGCGGCCGCCGTTTTACAAC 3'
```

The oligonucleotides introduce a NotI site within the pBluescript sequence about 50 bp downstream of the KpnI site.

Subcloning into RCEP4

The LamG123-collagen/pBluescript plasmid was digested with NotI to give a 6 kb fragment, which was ligated into NotI digested & phosphatased pCEP4 (10.4 kb). pCep4 vector (Invitrogen Life Technologies) is commercially available and the sequence may be found at http://www.invitrogen.com. Correct orientation of the 6 kb NotI fragment into pCep4 was determined by DNA sequencing.

Using the cloning strategy outlined above the procollagen type III N-propeptide Sequence prior to N100 was replaced with the sequence for the G123 domains of the α3 chain of Laminin-5, whilst retaining the collagen III signal sequence. The entire nucleotide sequence of the DNA molecule is presented in FIG. 3 (and SEQ ID No. 9). FIG. 4 (and SEQ ID No. 10) represents the amino acid sequence of the modified pro-α chain (a molecule according to the first aspect of the invention) which may be expressed from the DNA molecule. The junction between the G123 of laminin and procollagen sequences is shown as underlined in FIGS. 3 and 4.

The DNA molecule sub-cloned into the expression vector PCEP4 was expressed in HBK293-EBNA cells (Invitrogen Life Technologies).

HEK293-EBNA cells are known to those skilled in the art and details are available from http://www.invitrogen.com/Content/Tech-Online/molecular_biology/manuals_pps/293ebna_man.pdf HEK293-EBNA cells do not secrete procollagens and so are ideal for a negative background to express collagens in. Importantly, these cells do contain prolyl 4-hydroxylase which is vital for the hydroxylation of proline residues in the procollagen sequence and hence for the stability of the triple helix. The HEK293-EBNA line also expresses the EBNA-1 antigen that ensures that any plasmid DNA transfected into the cell is maintained episomally when the presence of that plasmid is selected for by the appropriate antibiotic (generally hygromycin).

Modified pro-α chains according to the first aspect of the invention are generated in the endoplasmic reticulum of the HEK293-EBNA cells. These molecules then automatically form a homotrimer (modified procollagen molecules according to the third aspect of the invention). The modified procollagen molecule produced from said cells is hereinafter referred to LamG123-coll.

A Integra CL 350 flask was seeded with HEK293-EPNA cells transformed with the DNA molecule and left for 7 days. The enriched medium was then harvested three times weekly (days 7, 9, 12, 14 and 16 after seeding).

Figure 5:
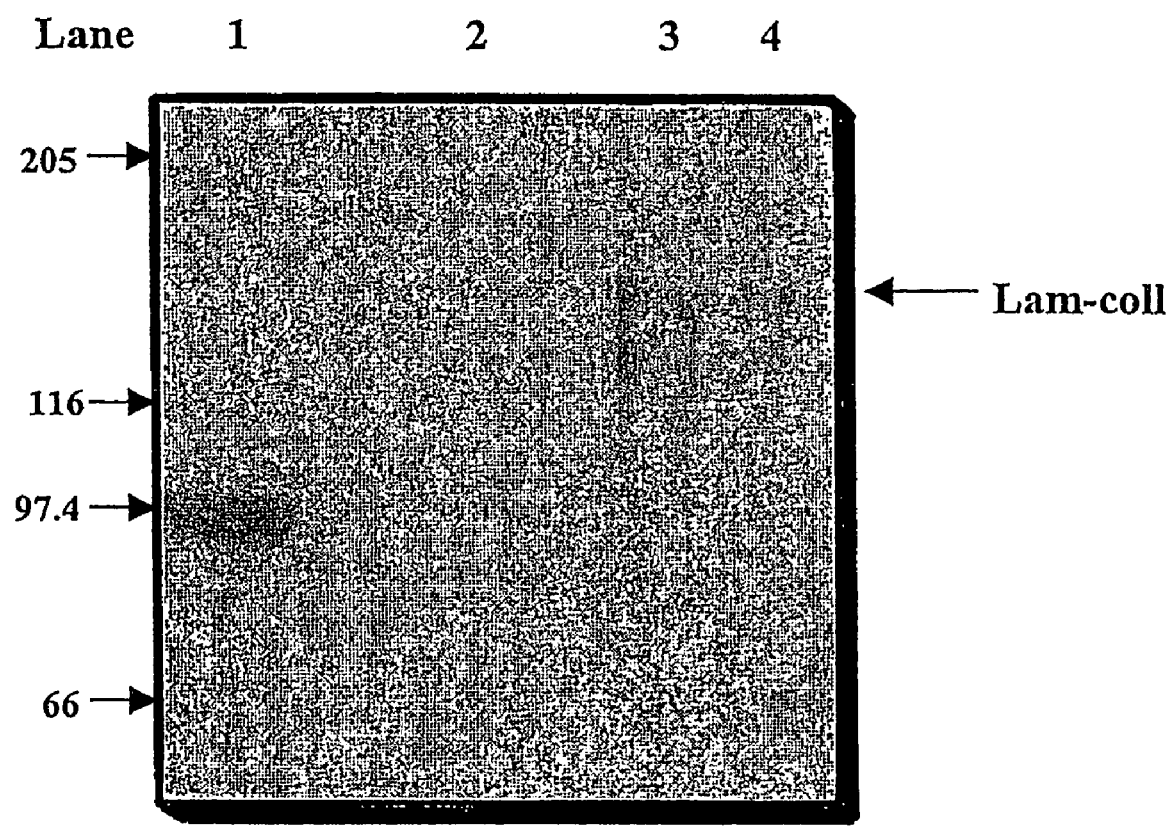
FIG. 5 is a photograph of a Western blot referred to in Examples 1 and 2.

LamG123-coll was characterised by Western blotting using an anti-collagen antibody. The results are presented in FIG. 5 of the accompanying drawings wherein Lane 1 is type III procollagen control, Lane 2 has medium from untransfected 293 cells, Lane 3 has medium from 293 EBNA cells transfected with LG123-coll and Lane 4 has medium from 293 EBNA cells transfected with LamG3-coll (see Example 2 below).

EXAMPLE 2

Design and Construction of a DNA Molecule According to the Second Aspect of the Invention, the Amino Acid Sequence of the Modified Pro-α Chain Expressed therefrom According to a First Aspect of the Invention and the Expression and Characterisation of Modified Procollagens Prepared therefrom According to a Third Aspect of the Invention A DNA molecule according to the second aspect of the invention was constructed comprising the coding region for the G3 domain of the α-3 chain of Laminin 5 in place of the globular domain of the N-propeptide of the proα1(III) chain.

The cloning strategy for production of the DNA molecule involved the following primary PCR reactions.
1. Substrate: pRMI containing the complete cDNA for pro-α1(III) chain of collagen (publicly available X 14420).
   Oligonucleotides:

```
T3 (5' end)                              (Seq ID. NO:1)
5' AATTAACCCTCACTAAAGGG 3'

SSLAMG3-2 (3' end)                       (Seq ID NO:11)
5' GCTTCCAGTCTTCCGAGCATGCCAAAATAATAGTGGG 3'
```

Product A: 300 bp.
2. Substrate: Lam5α3-pSECTAG2C containing gene for α3 chain cloned in on Asp718I site
   Oligonucleotides:

```
SLAMG3-1 (5' end)                        (Seq. ID NO:12)
5' CCCACTATTATTTTGGCATGCTCGGAAGACTGGAAGC 3'

LG3-20R (3' end)                         (Seq. ID NO:4)
5' CTTGACCATTAGCATCTTGCCACACCTTCAC 3'
```

Product B: 700 bp

The following secondary PCR Reaction was then carried out.
1) Substrate: Mixture of A (300 bp) and B (700 bp) products
   Oligonucleotides: T3 (5'end) LG3-20R (3'end)
   Product AB: 1.0 kb Cloning of AB Product into pBluescript Product AB was digested with HindIII and NotI and then ligated into pBS also digested with HindIII and NotI to generate G3AB-pBS plasmid.

Generation of Chimeric LamG-Collagen Gene

The G3AB-pBS plasmid was digested with Not1 and HindIII and the 200 bp fragment was gel purified. The G3AB-pBS plasmid was digested with BamH1 and HindIII and the 1.36 kb fragment was gel purified. The pRMI plasmid was digested with Not1 and BamH1 and the 6.8 kb fragment was gel purified.

The three fragments were ligated together to generate the gene encoding the LamG3-collagen fusion protein. Correct assembly of the lamG3-collagen gene was determined by DNA sequencing.

Modification of the LamG3-Collagen/pBluescript Plasmid

A NotI site was introduced 3' to the collagen sequence by standard PCR mediated site-directed mutagenesis using the oligonucleotides TAS14NotA and Oligo32merTAS12NotS, (see Example 1 above)

The oligonucleotides introduce a NotI site within the pbluescript sequence about 50 bp downstream of the KpnI site.

Subcloning into pCEP4

The LamG3-collagen/pBluescript plasmid was digested with NotI to give a 5 kb fragment, which was ligated into NotI digested & phosphatased pCEP4 (10.4 kb). Correct orientation of the 5 kb NotI fragment into pCep4 was determined by DNA sequencing.

Using the cloning strategy outlined above the procollagen type III N-propeptide Sequence prior to N100 was replaced with the sequence for the G3 domain of the α3 chain of Laminin-5, whilst retaining the collagen III signal sequence. The entire nucleotide sequence of the DNA molecule is presented in FIG. 6 (and SEQ ID No. 13). FIG. 7 (and SEQ ID No. 14) represents the amino acid sequence of the modified pro-α chain (a molecule according to the first aspect of the invention) which may be expressed from the DNA molecule. The junction between the G3 of laminin and procollagen sequences is shown as underlined in FIGS. 6 and 7.

The DNA molecule sub-cloned into the expression vector PCEP4 was expressed in HEK293-EBNA cells (Invitrogen Life Technologies).

Modified pro-α chains according to the first aspect of the invention are generated in the endoplasmic reticulum of the HEK293-EBNA cells. These molecules then automatically form a homotrimer (modified procollagen molecules according to the third aspect of the invention). The modified procollagen molecule produced from said cells is hereinafter referred to LamG3-coll.

A Integra CL 350 flask was seeded with HEK293-EPNA cells transformed with the DNA molecule from this Example and left for 7 days. The enriched medium was then harvested three times weekly (days 7, 9, 12, 14 and 16 after seeding).

LamG3-coll was characterised by Western blotting using an anti-collagen antibody. The results are presented in FIG. 5 wherein Lane 4 has medium from 293 EBNA cells transfected with LamG3-coll.

EXAMPLE 3

Design and Construction of a DNA Molecule According to the Second Aspect of the Invention, the Amino Acid Sequence of the Modified Pro-α Chain Expressed therefrom According to a First Aspect of the Invention and the Expression and Characterisation of Modified Procollagens Prepared therefrom According to a Third Aspect of the Invention A DNA molecule according to the second aspect of the invention was constructed comprising the entire coding region for secretory leukocyte protease inhibitor precursor ("SLPI") in place of the globular domain of the N-propeptide of the proα1(III) chain. "SLPI-Collagen" (or slpi-coll) was produced by constructing the SLPICollagenIII/pCEP4 construct, involving polymerase chain reactions, restriction digestion and ligation.

Polymerase Chain Reactions

The Platinum® Pfx DNA polymerase (Invitrogen, U.K.), the corresponding recipe and cycling programme as recommended by the manufacturer were used for all the PCRs carried out in cloning SLPI-Collagen. Three rounds of PCR were required for the assembly of SLPI-CollagenIII/pCEP4 construct.

In the first round, the sequence encoding human SLPI was amplified from the image clone 4733996 (UK Human Genome Mapping Project Resource Centre, U.K.). The following primers were employed in the PCR:

```
5' primer                              (Seq ID NO:15)
5'-CTTGTAGATGCGGCCGCatgaagtccagcggcctctt-3'

3' primer                              (Seq ID NO:16)
5'-cttcaacagcagctttcacaggggaaacgc-3'
```

The primers resulted in the SLPI PCR products containing a Not I restriction site (GCGGCCGC) at the 5' end, indicated by bold capital letters in the sequence above, and at its 3' end, there were 10 base pairs encoding the 5' end of human type m collagen, indicated by italic small letter in the sequence above. The annealing temperature was 48° C. The PCR product was expected to have a size of 0.42 kilo basepairs (kbp). It was then gel purified using Qiagen Gel Extraction Kit (Qiagen, U.K.).

In the second round of PCR, part of the sequences encoding human type III collagen was amplified from the construct pRMI using the following primers:

```
5' primer                              (Seq ID NO:17)
5'-tgtgaaagctgctgttgaaggaggatgttc-3'

3' primer                              (Seq ID NO:18)
5'-ggacctggtcgaccactttc-3'
```

The italic small letters indicate nucleotides encoding SLPI. The annealing temperature was 50° C. pRMI is a pBluescript SK (-) vector carrying a human type III collagen insert. As a result, the 5' end of the PCR product had 10 base pairs encoding the 3' end of SLPI. The expected size of the Collagen III PCR product was 1.603 kbp. It was then gel purified using Qiagen Gel Extraction Kit (Qiagen).

In the third round of PCR, the sequences encoding SLPI-Collagen III fragment were amplified from the purified SLPI and Collagen III PCR products. The following primers were used:

```
5' primer                              (Seq ID NO:17)
5'-tgtgaaagctgctgttgaaggaggatgttc-3'

3' primer                              (Seq ID NO:18)
5'-ggacctggtcgaccactttc-3'
```

The resulting PCR product was expected to have a size of 2.023 kbp. It also contained a Not I and a Xma I restriction sites. It was then gel purified by the Qiagen gel extraction kit.

Restriction, Digestion and Ligation.

The purified SLPI-Collagen III PCR product was digested with restriction enzymes (Roche, U.K.) Not I and Xma I while the vector pRMI was digested with Not I and EcoR V followed by Xma I. The digests were then gel purified by the Qiagen gel extraction kit and this was followed by the dephosphorylation of the vector digest with alkaline phosphatase. Upon assessing the yield of the inserts and the dephosphorylated vector, a ligation reaction was set up using high concentration T4 DNA ligase (New Englands Biolabs, U.K.), according to manufacturer's instruction.

Transformation and Colony Screening.

5 µl of the ligation reaction was transformed into the chemically competent DH5α cells. The DNA from each colony was extracted by Qiagen miniprep kit (Qiagen). A positive clone was distinguished by restriction digestion with Xho I, yielding fragments of the right sizes on the agarose gel (1.936, 2.520 and 4.680 kbp).

Sequencing of the PCR Product.

Once a positive clone was identified, sequencing reactions were carried out to ensure that no error was introduced into the PCR product by the polymerase. The primers used in the sequencing reaction are shown below:

```
SK-T7                                  (Seq ID NO:19)
5'-gta ata cga ctc act ata ggg c-3'

C3For1                                 (Seq ID NO:20)
5'-gct gtt gaa gga gga tgt-3'

C3For2                                 (Seq ID NO:21)
5'-aga ggc ttc gat gga cga-3'

C3For3                                 (Seq ID NO:22)
5'-gga ctg cga ggt ggt gca-3'
```

-continued

```
C3Rev1                                  (Seq ID NO:23)
5'-ttc tcc cag gaa tac cag-3'

C3Rev2                                  (Seq ID NO:24)
5'-agg gaa tcc ggc agt tcc-3'

C3Rev3                                  (Seq ID NO:25)
5'-ctc ggg gac cag atg gcc-3'
```

Subcloning of SLPI-Collagen III PCR Product into p CEP4.

In order to subclone SLPI-Collagen III into pCEP4, SLPI-Collagen III/SK (+) was digested with Not I. This was followed by filling ends with Klenow (Roche) and restriction digestion with Hind III. The same procedures were performed on the vector pCEP4 except Not I was substituted by Kpn I. The insert and vector were then gel purified using the Qiagen gel extraction kit (Qiagen). In order to prevent self-ligation, the vector was also dephosphorylated with alkaline phosphatase (Roche).

A ligation react¹ion using high concentration T4 DNA ligase (NEB) was set up after the yields of the insert and vector were assessed. Chemically competent DH5α cells were then transformed with the construct. The DNA from each colony was extracted with Qiagen miniprep kit (Qiagen). Upon digestion with Xho I, a positive clone was revealed by the sizes of the DNA fragments obtained (1.924, 2.520 and 11.480 kbp).

Using the cloning strategy outlined above the procollagen type III N-propeptide sequence was replaced with the sequence for SLPI whilst retaining the collagen III signal sequence. The entire nucleotide sequence of the DNA molecule is presented in FIG. 8 (and SEQ ID No. 26). FIG. 9 (and SEQ ID No. 27) represents the amino acid sequence of the modified pro-α chain (a molecule according to the first aspect of the invention) which may be expressed from the DNA molecule. The underlined sections in FIGS. 8 and 9 relate to the DNA and amino acid sequence of SLPI respectively, whilst the non-underlined sections refer to DNA and amino acid sequences for human procollagen III starting from the von Willebrand Factor.

Figure 10:
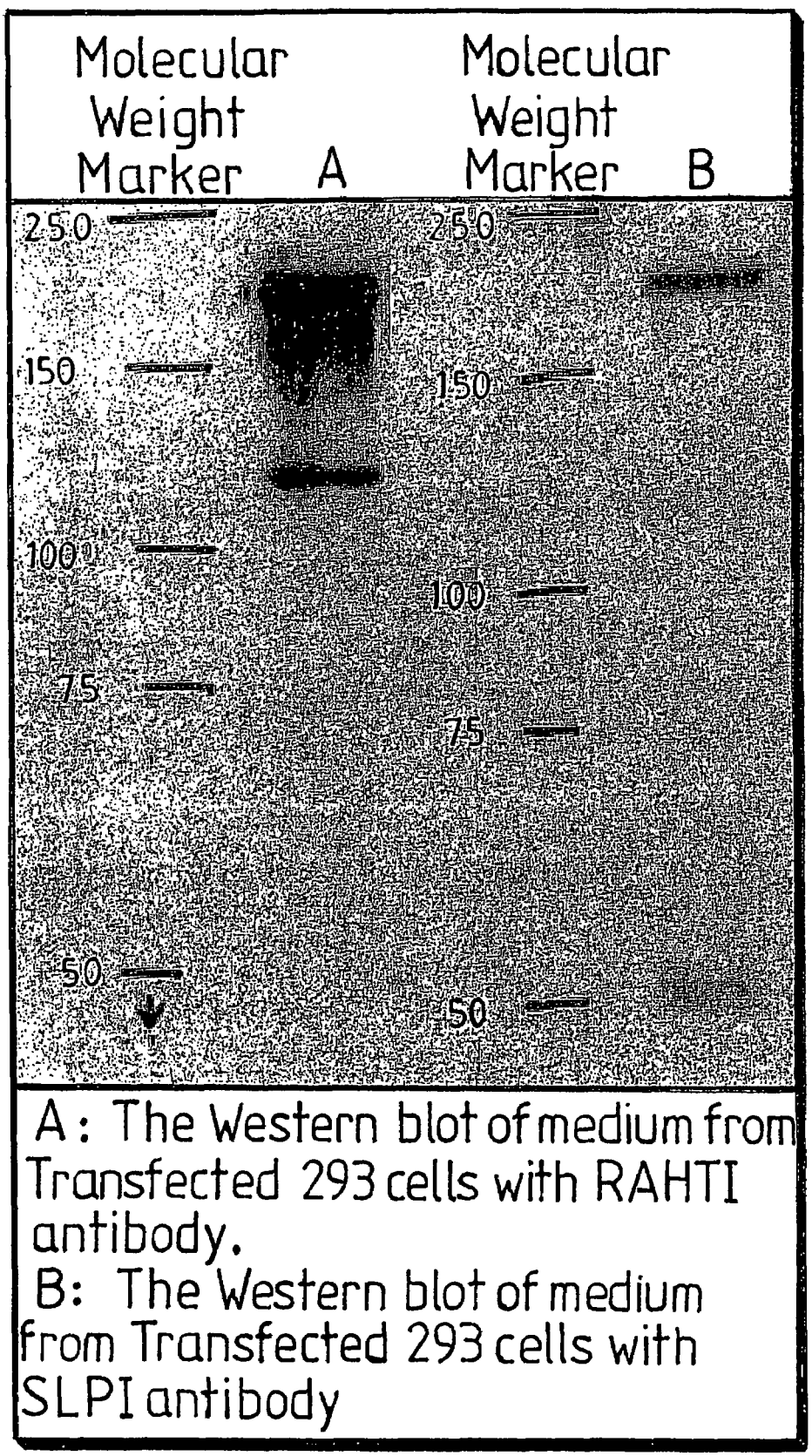
FIG. 10 is a photograph of a Western Blot referred to in Example 3.

The DNA molecule cloned into the pCEP4 vector was expressed in HEK 293 Ebna cells, see FIG. 10. The band for slpi-col is the single band in the western blotted into anti-slpi antibody.

The above Examples illustrate that modified collagens may be produced that contain part or all of a laminin or SLPI molecule. These modified domains are able to impart specific desirable functional characteristics to the collagen to enhance the wound healing properties of the molecule.

The invention claimed is:

1. A modified pro-α chain comprising at least part of a laminin glycoprotein wherein the at least part of a laminin glycoprotein is placed N-terminal to a triple helical forming domain of the pro-α chain.

2. The modified pro-α chain as claimed in claim 1 wherein the triple helical forming domain is from a fibrillar forming pro-α chain.

3. The modified pro-α chain as claimed in claim 2 wherein the triple helical forming domain is from a type I, II, III, V or XI pro-α chain.

4. The modified pro-α chain as claimed in claim 3 wherein the triple helical forming domain is from a pro-α chain.

5. The modified pro-α chain as claimed in claim 4 wherein the pro-α chain further comprises a procollagen N-propeptide sequence, wherein the procollagen N-terminal sequence is replaced prior to N100 with the sequence for the laminin glycoprotein.

6. The modified pro-α chain as claimed in claim 5 wherein a N- proteinase cleavage site associated with the N-terminal propeptide domain is modified such as to alter the domain's susceptibility to cleavage.

7. The modified pro-α chain as claimed in claim 1, wherein the laminin glycoprotein comprises the globular domains of an α-chain of a laminin molecule.

8. The modified pro-α chain as claimed in claim 7 wherein the globular domain is derived from the globular chain of Laminin-5.

9. The modified pro-α chain as claimed in claim 7, wherein the pro-α chain further comprises a procollagen N-propeptide sequence, wherein the procollagen N-terminal sequence is replaced prior to N100 with the sequence for the laminin glycoprotein.

10. The modified pro-α chain as claimed in claim 7 wherein the laminin glycoprotein comprises the amino acid sequence for at least the G3 globular domain of the α-chain of a laminin molecule.

11. The modified pro-α chain as claimed in claim 10 wherein the globular domain is derived from the globular chain of Laminin-5.

12. The modified pro-α chain as claimed in claim 10 wherein the laminin glycoprotein contains the amino acids of SEQ ID NO: 14.

13. The modified pro-α chain as claimed in claim 10 wherein the pro-α chain further comprises a procollagen N-propeptide sequence, wherein the procollagen N-terminal sequence is replaced prior to N100 with the sequence for the laminin glycoprotein.

14. The modified pro-α chain as claimed in claim 13 wherein a N- proteinase cleavage site associated with the N-terminal propeptide domain is modified such as to alter the domain's susceptibilily to cleavage.

15. The modified pro- α chain as claimed in claim 7 wherein the laminin glycoprotein comprises the amino acid sequence for the G1 to G3 domains of the α-chain of a laminin molecule.

16. The modified pro-α chain as claimed in claim 15 wherein the globular domains are derived from the globular chain of Laminin-5.

17. The modified pro-α chain as claimed in claim 15 wherein the laminin glycoprotein contains the amino acids of SEQ ID NO: 10.

18. The modified pro-α chain as claimed in claim 1, wherein the laminin glycoprotein comprises at least part of the globular domains of Laminin-5.

19. The modified pro-α chain as claimed in claim 1 further comprising a procollagen N-propeptide sequence, wherein the procollagen N-propeptide sequence is replaced prior to N100 within the sequence for the laminin glycoprotein.

20. The modified pro-α chain as claimed in claim 19 wherein a N-proteinase cleavage site associated with the N-terminal propeptide domain is modified such as to alter the domain's susceptibility to cleavage.

21. The modified pro-α chain as claimed in claim 19, wherein a N-proteinase cleavage site associated within the N-terminal propeptide domain is modified such as to alter the domain's susceptibility to cleavage.

22. The modified pro-α chain as claimed in claim 21 wherein the N-proteinase cleavage site is modified such that the domain may not be cleaved.

23. The modified pro-α chain as claimed in claim 22 wherein a region between the triple helical forming domain and the N-propeptide forming domain of the pro-α chain is modified to confer resistance to N-proteinases.

24. The modified pro-α chain as claimed in claim 23 wherein Pro-Gln in the region is altered to Leu-Pro.

25. A procollagen molecule comprising a trimer of pro-α chains characterised in that at least one of the pro-α chains is a modified pro-α chain as defined by claim 24.

26. A procollagen molecule comprising a trimer of pro-α chains characterized in that at least one of the pro-α chains is a modified pro-α chain as defined by claim 1.

27. A procollagen molecule as claimed in claim 26 wherein the pro-α chain is truncated C-terminal to the triple helical domain.

28. A procollagen molecule comprising a trimer of pro-α chains characterised in that at least one of the pro-α chains is a modified pro-α chain as defined by claim 4.

29. A procollagen molecule comprising a trimer of pro-α chains wherein the molecule includes one of SEQ ID NO: 10 or SEQ ID NO: 14.

30. A collagen matrix comprising the procollagen molecule as defined by claim 26.

31. A collagen matrix comprising collagen monomers having modified propeptide domains derived from procollagen molecules as defined by claim 27.

32. A collagen polymer comprising at least one modified collagen monomer, wherein said modified collagen monomer comprises at least part of a laminin glycoprotein placed N-terminal to a triple helical forming domain in a collagen monomer.

33. A dressing comprising the procollagen molecules as defined by claim 26.

34. A dressing comprising a collagen matrix as defined by claim 30.

35. A DNA molecule encoding the modified pro-α chain as defined by claim 1.

36. A vector comprising the DNA of claim 35.

37. The vector of claim 36 wherein the vector is a plasmid, cosmid or phage.

38. The vector of claim 36 wherein the vector comprises a selectable marker.

39. A host cell comprising the vector of claim 36.

40. The host cell of claim 39 wherein the host cell is a mammalian cell.

41. The host cell of claim 39 wherein the host cell is selected from the HEK293 cell line.

42. The DNA molecule encoding modified pro-α chain as claimed in claim 35 characterized in that the molecule includes the bases of SEQ ID NO: 9.

43. The DNA molecule encoding modified pro-α chain as claimed in claim 35 characterized in that the molecule includes the bases of SEQ ID NO: 13.

44. A DNA molecule encoding modified pro-α chain as defined in claim 1, said modified pro-α chain comprising the amino acids of one of SEQ ID NO: 10 or SEQ ID NO: 14.

45. A vector comprising the DNA of claim 44.

46. The vector of claim 45 wherein the vector is a plasmid, cosmid or phage.

47. The vector of claim 45 wherein the vector comprises a selectable marker.

48. A host cell comprising the vector of claim 45.

49. The host cell of claim 48 wherein the host cell is a mammalian cell.

50. The host cell of claim 48 wherein the host cell is selected from the HEK293 cell line.

51. A DNA molecule encoding modified pro-α chain as defined by claim 4.

52. A vector comprising the DNA of claim 51.

53. The vector of claim 52 wherein the vector is a plasmid, cosmid or phage.

54. The vector of claim 52 wherein the vector comprises a selectable marker.

55. A host cell comprising the vector of claim 52.

56. The host cell of claim 55 wherein the host cell is a mammalian cell.

57. The host cell of claim 55 wherein the host cell is selected from the HEK293 cell line.

58. A DNA molecule encoding modified pro-α chain as defined by claim 11.

59. A vector comprising the DNA of claim 58.

60. The vector of claim 59 wherein the vector is a plasmid, cosmid or phage.

61. The vector of claim 59 wherein the vector comprises a selectable marker.

62. A host cell comprising the vector of claim 59.

63. The host cell of claim 62 wherein the host cell is a mammalian cell.

64. The host cell of claim 62 wherein the host cell is selected from the HEK293 cell line.

65. A DNA molecule encoding modified pro-α chain as defined by claim 24.

66. A vector comprising the DNA of claim 65.

67. The vector of claim 66 wherein the vector is a plasmid, cosmid or phage.

68. The vector of claim 66 wherein the vector comprises a selectable marker.

69. A host cell comprising the vector of claim 66.

70. The host cell of claim 69 wherein the host cell is a mammalian cell.

71. The host cell of claim 70 wherein the host cell is selected from the HEK293 cell line.

72. A medicament comprising the modified pro-α chain according to claim 1 for use in the treatment of wounds or fibrotic disorders.

73. A medicament comprising the modified pro-α chain according to claim 4 for use in the treatment of wounds or fibrotic disorders.

74. A medicament comprising the modified pro-α chain according to claim 11 for use in the treatment of wounds or fibrotic disorders.

75. A medicament comprising the modified pro-α chain according to claim 24 for use in the treatment of wounds or fibrotic disorders.

76. A medicament comprising the procollagen molecule according to claim 29 for use in the treatment of wounds or fibrotic disorders.

77. A medicament comprising the collagen matrix according to claim 30 for use in the treatment of wounds or fibrotic disorders.

78. A medicament comprising the collagen matrix according to claim 31 for use in the treatment of wounds or fibrotic disorders.

79. A medicament comprising the collagen polymer according to claim 32 for use in the treatment of wounds or fibrotic disorders.

80. A method of treating a wound or fibrotic disorder comprising administering to a subject in need of such treatment a therapeutically effective amount of a modified pro-α chain according to claim 1.

81. A method of treating a wound or fibrotic disorder comprising administering to a subject in need of such treatment a therapeutically effective amount of a modified pro-α chain according to claim 4.

82. A method of treating a wound or fibrotic disorder comprising administering to a subject in need of such treatment a therapeutically effective amount of a modified pro-α chain according to claim 11.

83. A method of treating a wound or fibrotic disorder comprising administering to a subject in need of such treatment a therapeutically effective amount of a modified pro-α chain according to claim 24.

84. A method of treating a wound or fibrotic disorder comprising administering to a subject in need of such treatment a therapeutically effective amount of a procollagen molecule according to claim 29.

85. A method of treating a wound or fibrotic disorder comprising administering to a subject in need of such treatment a therapeutically effective amount of a collagen matrix according to claim 30.

86. A method of treating a wound or fibrotic disorder comprising administering to a subject in need of such treatment a therapeutically effective amount of a collagen matrix according to claim 31.

87. A method of treating a wound or fibrotic disorder comprising administering to a subject in need of such treatment a therapeutically effective amount of a collagen polymer according to claim 32.

88. A method of treating a wound or fibrotic disorder comprising applying to a subject in need of such treatment the dressing according to claim 34.

* * * * *